United States Patent
Shimizu et al.

(10) Patent No.: US 11,911,366 B2
(45) Date of Patent: Feb. 27, 2024

(54) PHARMACEUTICAL COMPOSITION FOR ORAL ADMINISTRATION OF EDARAVONE AND METHOD OF ADMINISTERING SAME

(71) Applicant: MITSUBISHI TANABE PHARMA CORPORATION, Osaka (JP)

(72) Inventors: Hidetoshi Shimizu, Osaka (JP); Yoshinobu Nakamaru, Osaka (JP); Yukiko Nishimura, Osaka (JP)

(73) Assignee: MITSUBISHI TANABE PHARMA CORPORATION, Osaka (JP)

( * ) Notice: Subject to any disclaimer, the term of this patent is extended or adjusted under 35 U.S.C. 154(b) by 0 days.

(21) Appl. No.: 17/564,538

(22) Filed: Dec. 29, 2021

(65) Prior Publication Data

US 2022/0142982 A1 May 12, 2022

Related U.S. Application Data

(63) Continuation of application No. PCT/JP2021/041673, filed on Nov. 12, 2021.

(30) Foreign Application Priority Data

Nov. 12, 2020 (JP) ................................. 2020-188514

(51) Int. Cl.
  *A61K 31/4152* (2006.01)
  *A61K 9/24* (2006.01)
  *A61P 25/28* (2006.01)
  *A61K 9/00* (2006.01)

(52) U.S. Cl.
  CPC ........ *A61K 31/4152* (2013.01); *A61K 9/0024* (2013.01); *A61K 9/0053* (2013.01); *A61P 25/28* (2018.01)

(58) Field of Classification Search
  CPC .............. A61K 31/4152; A61K 9/0024; A61K 9/0053; A61P 25/28
  See application file for complete search history.

(56) References Cited

U.S. PATENT DOCUMENTS

2019/0083463 A1* 3/2019 Zhou .................... A61K 9/1075
2019/0328712 A1* 10/2019 Moolenaar ............. A61K 47/26

FOREIGN PATENT DOCUMENTS

| JP | H05-031523 B | 5/1993 |
| JP | 3758164 B | 3/2006 |
| JP | WO 2020/091036 A | 9/2021 |

OTHER PUBLICATIONS https://www.sps.nhs.uk/medicines/edaravone/, Edaravone published Aug. 30, 2016, by Mitsubishi Tanabe. (Year: 2016).*
Sutton et al., "The impact of gastric pH, volume, and emptying on the food effect of ziprasidone oral absorption," The AAPS Journal vol. 19, No. 4, Jul. 2017. (Year: 2017).*
Takei K et al., Radicava (edaravone) for amyotrophic lateral sclerosis: new formulation and its development plan, Amyotrophic Lateral Sclerosis and Frontotemporal Degeneration, 2018, vol. 19(Supple. S1), pp. 272.
Wu, et al., "Predicting Drug Disposition via Application of BCS: Transport/Absorption/Elimination Interplay and Development of a Biopharmaceutics Drug Disposition Classification System", Pharmaceutical Research, vol. 22, No. 1, Jan. 2005, pp. 11-23.
Takei, et al., "Radicava® (edaravone) for Amyotrophic Lateral Sclerosis: New Formulation and Its Development Plan (P1.4-014)", Neurology, American Academy of Neurology, first published Apr. 16, 2019.
FDA Guideline, "Assessing the Effects of Food on Drugs in INDs and NDAs—Clinical Pharmacology Considerations, Guidance for Industry", Feb. 2019.

* cited by examiner

*Primary Examiner* — Jared Barsky
(74) *Attorney, Agent, or Firm* — Oblon, McClelland, Maier & Neustadt, L.L.P.

(57) ABSTRACT

A method of treating an oxidative stress disease includes orally or intragastrically administering, to a subject in need thereof, a pharmaceutical composition including edaravone with a time interval from a consumption of a meal by the subject in need thereof to an administration of the pharmaceutical composition to the subject in need thereof. The time interval is 8 hours or longer after the consumption of a high-fat meal, the time interval is 4 hours or longer after the consumption of a standard meal, or the time interval is 2 hours or longer after the consumption of a light meal.

14 Claims, 2 Drawing Sheets

PHARMACEUTICAL COMPOSITION FOR ORAL ADMINISTRATION OF EDARAVONE AND METHOD OF ADMINISTERING SAME

CROSS-REFERENCE TO RELATED APPLICATIONS

The present application is a bypass continuation of International Application No. PCT/JP2021/041673, filed Nov. 12, 2021, which is based upon and claims the benefit of priority to Japanese Application No. 2020-188514, filed Nov. 12, 2020. The entire contents of these applications are incorporated herein by reference.

BACKGROUND OF THE INVENTION

Field of the Invention

The present invention relates to a pharmaceutical composition containing edaravone as an active ingredient for oral administration or for intragastric administration.

Description of Background Art

Edaravone is 3-methyl-1-phenyl-2-pyrazolin-5-one of a formula below, and its pharmaceutical applications include a therapeutic agent or a brain function normalizing agent for oxidative stress diseases, such as amyotrophic lateral sclerosis (ALS) (JP 05-031523 B and JP 3758164 B).

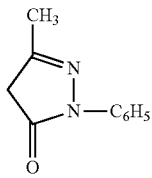

ALS is an intractable disease with an initial symptom including weakness of the hands, dyskinesia of the fingers, and fasciculation of the upper limbs, and followed by a symptom such as muscle atrophy, muscle weakness, bulbar palsy, and muscular fasciculation, ALS leads to respiratory failure. Based on the site of onset, ALS is classified into an upper limb type, a bulbar type, a lower limb type, and a mixed type, all of which affect muscle groups throughout the body as symptoms progress. Although the etiology of ALS has not yet been fully elucidated, the following hypotheses have been presented as the major etiology: (1) autoimmunity (appearance of autoantibodies against a Ca channel), (2) excitatory amino acid excess and poisoning (increase in extracellular glutamic acid and impaired glutamic acid transport), (3) oxidative stress disorder (neuronopathy due to Cu/Zn superoxide dismutase (SOD) gene abnormality and free radicals), (4) cytoskeletal damage (accumulation of neurofilaments and appearance of inclusion bodies in motor nerve cells), and (5) neurotrophic factor deficiency. Edaravone is used as a therapeutic agent for ALS and is available only in the form of an injectable agent. The entire contents of these publications are incorporated herein by reference.

SUMMARY OF THE INVENTION

According to one aspect of the present invention, a method of treating an oxidative stress disease includes orally or intragastrically administering, to a subject in need thereof, a pharmaceutical composition including edaravone with a time interval from a consumption of a meal by the subject in need thereof to an administration of the pharmaceutical composition to the subject in need thereof. The time interval is 8 hours or longer after the consumption of a high-fat meal, the time interval is 4 hours or longer after the consumption of a standard meal, or the time interval is 2 hours or longer after the consumption of a light meal.

According to another aspect of the present invention, a method of administering a pharmaceutical composition including edaravone includes orally or intragastrically administering, to a subject in need thereof, a pharmaceutical composition including edaravone with a time interval from a consumption of a meal by the subject in need thereof to an administration of the pharmaceutical composition to the subject in need thereof. The time interval is 8 hours or longer after the consumption of a high-fat meal, the time interval is 4 hours or longer after the consumption of a standard meal, or the time interval is 2 hours or longer after the consumption of a light meal.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
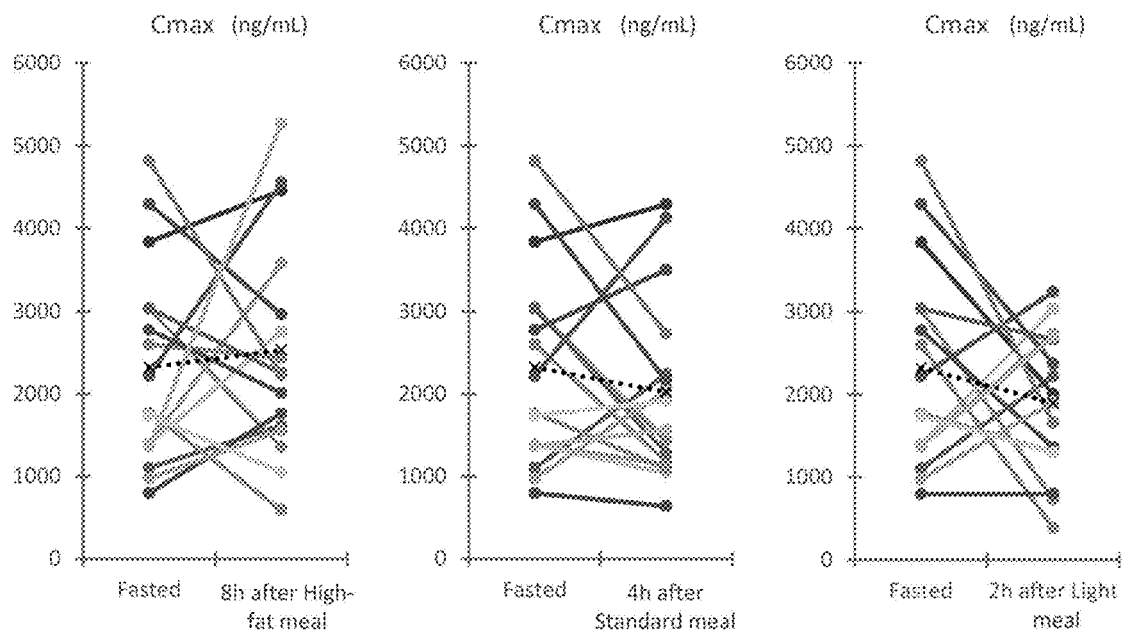
FIG. 1 shows spaghetti plots comparing the Cmax after administration of edaravone oral formulation between a fasted group, a group administered 8 hours after high-fat meal consumption, a group administered 4 hours after standard meal consumption, and a group administered 2 hours after light meal consumption (The circles with solid lines represent individual values, and the crosses with dotted lines represent mean values)

Embodiments of the present invention will be described with reference to specific examples; however, the present invention is not limited to these examples.

A pharmaceutical composition according to an embodiment of the present invention and a method of administration according to an embodiment of the present invention include the conditions for the administration timing in which the pharmaceutical composition is administered with time intervals according to the types of meals, and other conditions and processes are not particularly limited. Specifically, the excellent effect of avoiding influence from a meal on the pharmacokinetics of edaravone is achieved by the administration timing. Thus, for example, the edaravone content and composition in a pharmaceutical composition according to an embodiment of the present invention is not particularly limited. In an embodiment of the present invention, the types of meals are classified, for example, based on calories.

In the present specification, "first time interval" means a time from meal consumption to an administration, and for example, it may be referred as "pre-administration time interval" or "after-meal/before-administration time interval." "Second time interval" means a time from an administration to meal consumption, and for example, it may be referred as "post-administration time interval" or "after-administration/before-meal time interval." The terms "first" and "second" in the "first time interval" and the "second time interval" are used to distinguish the two different time intervals and do not indicate the order, for example. "Oral administration" means administering a drug from the mouth, and "intragastric administration" means administering a drug directly to the stomach. In addition, the pharmaceutical composition according to an embodiment of the present invention is a pharmaceutical composition for use in such oral administration or intragastric administration. In the use of the pharmaceutical composition according to an embodiment of the present invention and in the administration method according to an embodiment of the present invention, for example, the type of instrument, device, or the like when used for oral administration or intragastric administration is not particularly limited. For intragastric administration, for example, a tube such as a feeding tube can be used, and the tube is also referred as, for example, a catheter. The intragastric administration via the tube is also referred as, for example, transluminal administration or intragastric transluminal administration. Examples of the intragastric administration include administration via a gastrostomy tube and nasogastric administration. The administration via a gastrostomy tube is, for example, a method of perforating the stomach (performing gastrostomy), passing the tube through the perforation (gastric fistula), and administering a drug directly into the stomach. A tube to be used for the administration via a gastric fistula includes, for example, a gastric fistula catheter (hereinafter, it may be referred as "gastric fistula tube," "feeding tube," "nutrition connection tube," "connection tube," "percutaneous endoscopic gastrostomy (PEG) catheter" or "percutaneous endoscopic gastrostomy (PEG) tube"). In addition, the nasogastric administration is, for example, a method of passing a tube from the nose into the stomach and administering a drug directly into the stomach. A tube to be used for the nasogastric administration includes, for example, a nasal gastric catheter (hereinafter, it may be referred as "nasal gastric tube," "nasal feeding tube," "nasal sonde," "nasal tube," "feeding catheter," "nasal feeding catheter," "gastric catheter" or "nasopharyngeal gastric (NG) tube"). The pharmaceutical composition according to an embodiment of the present invention is also referred to as, for example, a "transluminal formulation" when used for intragastric administration via the tube.

As described above, a pharmaceutical composition according to an embodiment of the present invention is characterized by containing edaravone as an active ingredient, and the pharmaceutical composition is administered orally or intragastrically with the most suitable one of the time intervals 1) to 3) described below for each type of meal.

The composition of the pharmaceutical composition according to an embodiment of the present invention is any composition containing edaravone as an active ingredient, and other constitution is not particularly limited. The pharmaceutical composition according to an embodiment of the present invention, for example, may contain only an active ingredient or may contain an active ingredient and an additional excipient. The active ingredient may be, for example, only edaravone or may be edaravone in combination with another drug. In the pharmaceutical composition according to an embodiment of the present invention, the form of edaravone is not particularly limited, and examples include a particulate form (hereinafter also referred to as an "edaravone particle"). The additional excipient is not particularly limited, and examples include dispersants, such as polyvinyl alcohols and sucrose fatty acid esters; thickeners, such as xanthan gums and powdered tragacanth; sweeteners, such as sorbitol; stabilizers, such as sodium hydrogen sulfite and L-cysteine hydrochloride; pH adjusters, such as phosphoric acid, acetic acid, and sodium hydroxide; defoamers, such as simethicone emulsions; fillers, such as glucose and starch; solvents; and perfumes. Examples of the solvent include aqueous solvents, such as water, buffers, and saline; and oil solvents, such as olive oil.

Specific examples of a pharmaceutical composition according to an embodiment of the present invention include suspensions containing an edaravone particle, a dispersant, and water. The suspension is also referred to as, for example, an edaravone suspension for oral administration (which may be hereinafter referred to as the "edaravone oral formulation") or an edaravone suspension for intragastric administration (which may be hereinafter referred to as the "edaravone intragastric formulation"). A pharmaceutical composition according to an embodiment of the present invention is characterized by the administration timing as described above, and the composition is not limited. Thus, for the details of the composition of the pharmaceutical composition according to an embodiment of the present invention, the contents described in WO 2020/091036 are incorporated herein, and a pharmaceutical composition according to an embodiment of the present invention may be manufactured by the methods described in WO 2020/091036. Subjects of the administration of a pharmaceutical composition according to an embodiment of the present invention are, for example, humans or non-human animals and preferably humans. Non-human animals are, for example, mice, rats, rabbits, or horses.

The forms of a pharmaceutical composition according to an embodiment of the present invention are not particularly limited and may be, for example, a form suitable for oral administration, a form suitable for intragastric administration, or a form applicable to both oral administration and intragastric administration. The form is, for example, a liquid, a gel, or a solid. The liquid is exemplified by solutions and suspensions, the gel is exemplified by jellies, and the solid is exemplified by tablets, capsules, powders, fine granules, and granules. In an embodiment of the present invention, the preferred form is a liquid, and in particular, a suspension is preferred.

Examples of a pharmaceutical composition according to an embodiment of the present invention include compositions (1) to (5) exemplified below, preferably the composition (1) but not limited as such.

(1) Edaravone particle, polyvinyl alcohol (dispersant), xanthan gum (thickener), sorbitol (sweetener), sodium hydrogen sulfite (stabilizer), L-cysteine hydrochloride (stabilizer), phosphoric acid (pH adjuster), sodium hydroxide (pH adjuster), simethicone emulsion (defoamer), and water.

(2) Edaravone particle, polyvinyl alcohol (dispersant), powdered tragacanth (thickener), sorbitol (sweetener), sodium hydrogen sulfite (stabilizer), L-cysteine hydrochloride (stabilizer), phosphoric acid (pH adjuster), sodium hydroxide (pH adjuster), simethicone emulsion (defoamer), and water.

(3) Edaravone particle, sucrose fatty acid ester (dispersant), xanthan gum (thickener), sucrose (sweetener), sodium hydrogen sulfite (stabilizer), L-cysteine hydrochloride (stabilizer), acetic acid (pH adjuster), sodium hydroxide (pH adjuster), simethicone emulsion (defoamer), and water.

(4) Edaravone particle, polyvinyl alcohol (dispersant), xanthan gum (thickener), sorbitol (sweetener), sodium hydrogen sulfite (stabilizer), phosphoric acid (pH adjuster), sodium hydroxide (pH adjuster), simethicone emulsion (defoamer), and water.

(5) Edaravone particle, polyvinyl alcohol (dispersant), xanthan gum (thickener), sorbitol (sweetener), sodium hydrogen sulfite (stabilizer), L-cysteine hydrochloride (stabilizer), phosphoric acid (pH adjuster), sodium hydroxide (pH adjuster), simethicone emulsion (defoamer), perfume, and water.

More specifically, examples of the composition (1) include a suspension of the following composition. The suspension of the following composition has, for example, a total volume of 5 mL, an edaravone content of 105 mg, and a form of, for example, a liquid. However, the present invention is not limited as such.

Edaravone particle: 2.1% (w/v)
Polyvinyl alcohol (dispersant): 0.1% (w/v)
Xanthan gum (thickener): 0.3% (w/v)
Sorbitol (sweetener): 40% (w/v)
Sodium hydrogen sulfite (stabilizer): 0.1% (w/v)
L-Cysteine hydrochloride (stabilizer): 0.05% (w/v)
Sodium Hydroxide (pH adjuster): q.s.
Phosphoric acid (pH adjuster): q.s.
Simethicone emulsion (defoamer): 0.05% (w/v)
Dispersion medium: water
pH: from 2.5 to 6.0

A pharmaceutical composition according to an embodiment of the present invention avoids effects of meal consumption on the pharmacokinetics of edaravone in oral administration or intragastric administration of edaravone by varying the timing of administration according to the types of meals as described below, that is, setting the first time interval from consumption of a meal to administration to the condition 1), 2), or 3) described below. In an embodiment of the present invention, "avoid effects of meal consumption on the pharmacokinetics of edaravone" means, for example, maintaining the same pharmacokinetics as the pharmacokinetics when a pharmaceutical composition containing edaravone is administered under fasting conditions (e.g., fasting 10 hours or longer). Specifically, this means, for example, that in administration of the same pharmaceutical composition containing edaravone by the same method of oral administration or intragastric administration, the pharmacokinetics administered under the condition 1), 2), or 3) described below according to a meal maintains the same pharmacokinetics as the pharmacokinetics administered under the fasting conditions described below. In addition, "the same pharmacokinetics" means, for example, that the target pharmacokinetics is completely identical or in a range not significantly different. Specific examples include measuring the concentration of edaravone in plasma of a subject, for example, at a predetermined period before and after administration of the pharmaceutical composition containing edaravone. Then, "the same pharmacokinetics" means that comparison of the maximum plasma concentration (Cmax) and area under the curve (AUC) of edaravone with the Cmax and AUC in fasting for 10 hours or longer indicates no significant change and also the same level of distribution of individual values, or indicates statistically the same level to common criteria for bioequivalence (e.g., a least squares mean ratio and its 90% confidence interval are in the range of 0.8 to 1.25). Thus, according to an embodiment of the present invention, oral administration or intragastric administration of the pharmaceutical composition containing edaravone with the most suitable one of the administration intervals 1) to 3) described below according to the types of meals maintains the same pharmacokinetics as the pharmacokinetics when the pharmaceutical composition is administered in fasting conditions, for example, regardless of the formula of a pharmaceutical composition.

A pharmaceutical composition according to an embodiment of the present invention is administered to a subject orally or intragastrically with any one of the first time intervals 1) to 3) below, for example, according to the types of meals upon consuming a meal:

1) in a case where the subject has consumed a high-fat meal, 8 hours or longer after the consumption;
2) in a case where the subject has consumed a standard meal, 4 hours or longer after the consumption; and
3) in a case where the subject has consumed a light meal, 2 hours or longer after the consumption.

In a certain embodiment, a pharmaceutical composition according to an embodiment of the present invention is administered orally or intragastrically with a first time interval 2) or 3) described above, for example, according to the type of meal upon consuming a meal.

Furthermore, a pharmaceutical composition according to an embodiment of the present invention further effectively maintains the pharmacokinetics of edaravone, for example, by adjusting the second time interval until the next meal consumption after administration. The pharmaceutical composition according to an embodiment of the present invention may be administered with a second time interval from administration of the composition to the next meal consumption of, for example, 30 minutes or longer, preferably 1 hour or longer or 2 hours or longer. Specifically, the pharmaceutical composition according to an embodiment of the present invention may be administered with a second time interval of, for example, 30 minutes or longer, 1 hour or longer, or 2 hours or longer until the next consumption of a meal. In an embodiment of the present invention, the length of the second time interval after administration is not limited, for example, by the type of the next meal.

In a certain embodiment, a pharmaceutical composition according to an embodiment of the present invention is administered orally or intragastrically with any one of the first time intervals 1) to 3) described above and with a second time interval of 30 minutes or longer until the next meal consumption, for example, according to the type of meal upon consuming a meal.

In a certain embodiment, a pharmaceutical composition according to an embodiment of the present invention is administered orally or intragastrically with any one of the first time intervals 1) to 3) described above and with a second time interval of 1 hour or longer until the next meal consumption, for example, according to the type of meal upon consuming a meal.

In a certain embodiment, a pharmaceutical composition according to an embodiment of the present invention is administered orally or intragastrically with any one of the first time intervals 1) to 3) described above and with a second time interval of 2 hours or longer until the next meal consumption, for example, according to the type of meal upon consuming a meal.

In a certain embodiment, a pharmaceutical composition according to an embodiment of the present invention is administered orally or intragastrically with a first time interval 2) or 3) described above and with a second time interval of 30 minutes or longer until the next meal consumption, for example, according to the type of meal upon consuming a meal.

In a certain embodiment, a pharmaceutical composition according to an embodiment of the present invention is administered orally or intragastrically with a first time interval 2) or 3) described above and with a second time interval of 1 hour or longer until the next meal consumption, for example, according to the type of meal upon consuming a meal.

In a certain embodiment, a pharmaceutical composition according to an embodiment of the present invention is administered orally or intragastrically with a first time interval 2) or 3) described above and with a second time interval of 2 hours or longer until the next meal consumption, for example, according to the type of meal upon consuming a meal.

In an embodiment of the present invention, the high-fat meal, the standard meal, and the light meal are classified, for example, based on common classification criteria. Specifically, those are classified, for example, according to total calories of a single meal, and more specifically, those is classified, for example, according to the total calories and percentage of calories from lipid in the total calories.

The high-fat meal is primarily a meal classified as a high-fat meal and may contain, for example, a meal with calories approximating the upper limit side and lower limit side of the common reference value classified as a high fat meal.

Specifically, the high-fat meal in an embodiment of the present invention may contain, for example, in addition to a high-fat meal, a meal with calories less than reference calories for a high-fat meal and exceeding the reference calories for a standard meal in common classification criteria or may contain a meal with calories exceeding the reference calories for a high-fat meal. Applying thus the first time interval condition 1) described above not only to the high-fat meal but also to a meal with calories exceeding the reference calories for a standard meal effectively maintains the pharmacokinetics of edaravone administered orally or intragastrically also when a meal corresponding to a border between a high-fat meal and a standard meal is consumed. In addition, the same applies to a meal with calories exceeding the reference calories for a high-fat meal.

A common criterion for a high-fat meal is, for example, total calories per meal of 800 to 1000 kilocalories, and examples include a meal with total calories of 800 to 1000 kilocalories and calorie intake from lipid of 50%, or a meal with total calories of 800 to 1000 kilocalories and calorie intake from lipid of 500 to 600 kilocalories and calorie intake from carbohydrate of 250 kilocalories. In an embodiment of the present invention, in addition to the high-fat meal described above, for example, a meal with total calories greater than 500 kilocalories and less than 800 kilocalories can also be classified as the high-fat meal. In addition, in an embodiment of the present invention, for example, a meal with total calories greater than 1000 kilocalories can also be classified as the high-fat meal. Furthermore, in an embodiment of the present invention, the high-fat meal described above may be, for example, a meal described as the high-fat meal in the FDA guideline (Assessing the Effects of Food on Drugs in INDs and NDAs—Clinical Pharmacology Considerations) or a meal described as the high-fat meal in the EMA guideline (Guideline on the investigation of drug interactions).

In an embodiment of the present invention, for the unit of total calories, "kilocalories", one kilocalorie is defined as energy required for raising the temperature of one liter of water by 1° C. In addition, kilocalories in the present specification are synonymous with "calories" used for meals as described in the website of the U.S. Department of Agriculture (USDA) (https://www.nutrition.gov/expert-q-a) (see the section "What is the difference between calories and kilocalories?"). In the present specification, the calorific value is described in the unit "kilocalories" based on the former definition as described above. For example, the calorific value of 800 to 1000 kilocalories described in the present specification means a calorific value of 800 to 1000 calories according to the description of the U.S. Department of Agriculture (USDA).

The normal food is primarily a meal classified as a normal meal and may contain, for example, a meal with calories approximating the lower limit side of the common reference value classified as a standard meal. In addition, in the present specification, the normal meal may be referred to as a low-fat meal or a standard meal. Specifically, the standard meal in an embodiment of the present invention may contain, for example, in addition to a standard meal, a meal with calories less than reference calories for a standard meal and exceeding the reference calories for a light meal in common classification criteria. Applying thus the first time interval condition 2) described above not only to the standard meal but also to a meal with calories exceeding the reference calories for a light meal can effectively maintain the pharmacokinetics of edaravone administered orally or intragastrically also when a meal corresponding to a border between a standard meal and a light meal is consumed.

A common criterion for a standard meal is, for example, total calories per meal of 400 to 500 kilocalories, and examples include a meal with total calories of 400 to 500 kilocalories and calorie intake from lipid of 25%, or a meal with total calories of 400 to 500 kilocalories and calorie intake from lipid of 150 kilocalories. In an embodiment of the present invention, in addition to the standard meal described above, for example, a meal with total calories greater than 250 kilocalories and less than 400 kilocalories can also be classified as the standard meal. Furthermore, in an embodiment of the present invention, the standard meal described above may be, for example, a meal described as the low-fat meal in the FDA guideline (Assessing the Effects of Food on Drugs in INDs and NDAs—Clinical Pharmacology Considerations) or a meal described as the moderate meal in the EMA guideline (Guideline on the investigation of drug interactions).

The light food is primarily a meal classified as a light meal and may contain, for example, a meal with calories approximating the lower limit side of the common reference value classified as a light meal. In addition, in the present specification, the light meal may be referred as a calorie supplement, a nutrition supplement, a nutritional diet, an enteral nutrition, a protein amino acid preparation, an elemental diet, a digestive enteral nutrition, a digestive nutritional supplement, a semi-digestive enteral nutrition, a semi-digestive nutritional supplement, a nutritional supplement, a nutritional supplement, a nourishing beverage, a nutritional food or a nutritionally functional food.

Specifically, the light meal in an embodiment of the present invention may contain, for example, in addition to a light meal, a meal with calories less than reference calories for a light meal in common classification criteria. Applying thus the first time interval condition 3) described above not only to the light meal but also to a meal with calories below the reference calories for a light meal can effectively maintain the pharmacokinetics of edaravone administered orally or intragastrically also when a meal with calories below the reference calories for a light meal is consumed.

A common criterion for a light meal is, for example, a meal with a total calorie per meal of 250 kilocalories. Specific examples of the light meal include liquid type nutritional supplements with approximately 250 kilocalories (enteral nutritional supplement: Ensure Liquid (trade name)). This is used, for example, for nutritional retention for patients after surgery and tubal alimentation for patients with difficulty in meal consumption over a long period. In addition, in an embodiment of the present invention, in addition to the light meal with approximately 250 kilocalories described above, for example, a meal with total calories less than 250 kilocalories can also be classified as the light meal.

The method of administering the pharmaceutical composition according to an embodiment of the present invention is oral administration or intragastric administration, and may be either. In administering the pharmaceutical composition according to an embodiment of the present invention to a patient over multiple times, the administration may be intragastric administration only, oral administration only, a combination of intragastric administration and oral administration, a change from oral administration to intragastric administration, or a change from intragastric administration to oral administration. In general, intragastric administration is used as a measure for a case where nutrition cannot be consumed through the mouth because of dysphagia or the like. Thus, for example, for more effective treatment according to symptoms, the administration may be changed from oral administration to intragastric administration. In addition, in the intragastric administration, for example, the administration is intragastric administration via a tube (also referred to as translumnal administration or translumnal intragastric administration) as described above, and as a specific example, the administration may be administration via a percutaneous endoscopic gastrostomy tube (PEG tube), administration via a nasopharyngeal gastric tube (NG tube), a combination of both, or a change from one to the other.

A material of the catheter or tube is not particularly limited, and examples include a silicone, a polyvinyl chloride, or polyurethane. In the catheter or tube, the material of the button is, for example, a silicone, polyurethane, a silicone rubber, or the like, and examples of the material of the tubing include a polyvinyl chloride or a silicone rubber/polyacetal. In the catheter or tube, examples of a combination of the materials of the button and tubing include a combination of a silicone button and polyvinyl chloride tubing, a combination of a polyurethane button and polyvinyl chloride tubing, or a combination of a silicone rubber button and a silicone rubber/polyacetal tubing.

In an embodiment of the present invention, the active ingredient according to an embodiment of the present invention, edaravone, is administered orally or via a feeding tube in the form of the pharmaceutical composition according to an embodiment of the present invention. For the feeding tube, for example, a nasopharyngeal gastric tube (which may be referred to as an "NG tube") or a percutaneous endoscopic gastrostomy tube (which may be referred to as a "PEG tube") can be used, and the pharmaceutical composition is administered via this feeding tube. Examples of the feeding tube include those made of a silicone, a polyvinyl chloride (PVC), and/or polyurethane.

In an embodiment of the present invention, when the active ingredient according to an embodiment of the present invention, edaravone, is administered in the form of the pharmaceutical composition according to an embodiment of the present invention, the pharmaceutical composition is taken on an empty stomach under a fasting condition. In this embodiment, it is preferable not to consume a meal 1 hour after administration, and it is desirable to avoid consumption of a high-fat meal (from 800 to 1000 calories (synonymous with from 800 to 1000 kilocalories as defined in the present specification), fat 50%) 8 hours before administration, consumption of a low-fat meal (from 400 to 500 calories (synonymous with from 400 to 500 kilocalories as defined in the present specification), fat 25%) 4 hours before administration, or consumption of a caloric supplement (250 calories (synonymous with 250 kilocalories as defined in the present specification), e.g., ENSURE LIQUID (trade name)) 2 hours before administration.

In another embodiment of the present invention, when the active ingredient according to an embodiment of the present invention, edaravone, is administered in the form of the pharmaceutical composition according to an embodiment of the present invention, it is preferable that a patient is informed that edaravone needs to be taken on an empty stomach under a fasting condition in the morning and that the night before each administration, a meal at bedtime is stopped, and for 1 hour after administration, a meal is not consumed. In addition, for postprandial administration, it is preferable to fast 8 hours before administration when a high-fat meal (1000 calories (synonymous with 1000 kilocalories as defined in the present specification), 50% fat) is consumed or 4 hours before administration when a low-fat meal (standard meal) (400 calories (synonymous with 400 kilocalories as defined in the present specification), 25% fat) is consumed. As an alternative option, a patient may consume a caloric supplement (250 calories (synonymous with 250 kilocalories as defined in the present specification) (e.g., a protein drink)) 2 hours before administration.

In administering a pharmaceutical composition according to an embodiment of the present invention, consumption of water is not particularly limited. In oral administration, the pharmaceutical composition according to an embodiment of the present invention when it is solid is, for example, preferably administered together with water, and the pharmaceutical composition according to an embodiment of the present invention when it is liquid or gel may be administered, for example, without water or together with water. In the intragastric administration via a tube, for example, water is preferably injected from the tube (e.g., the PEG tube or NG tube) to wash in the pharmaceutical composition according to an embodiment of the present invention after administration.

A pharmaceutical composition according to an embodiment of the present invention avoids effects of a meal on the pharmacokinetics of edaravone upon oral administration or intragastric administration of edaravone as described above. Thus, the application of the pharmaceutical composition according to an embodiment of the present invention is oral administration or intragastric administration of edaravone, and the target disease and symptom are any of those on which edaravone can act directly or indirectly and not particularly limited. Specifically, the target disease and symptom are diseases or symptoms that can be treated, for example, by scavenging free radicals by edaravone.

The disease is, for example, an oxidative stress disease, specifically examples include neurodegenerative diseases with motor dysfunction, such as ALS, Parkinson's disease, and spinocerebellar degeneration; muscle diseases, such as muscular dystrophy; intracerebral neurodegenerative diseases exhibiting cognitive impairment, such as Alzheimer's disease; vascular disorders, such as cerebral infarction; systemic inflammatory diseases, such as multiple sclerosis and systemic scleroderma; or local inflammatory diseases, such as stomatitis. Of these, the disease is preferably ALS. In an embodiment of the present invention, treatment of the disease includes the meaning of, for example, alleviation of disease progression, cure of the disease, prevention of morbidity, and prevention of recurrence, and may mean treatment for symptoms due to the disease described above. In an embodiment of the present invention, the treatment for symptoms includes the meaning of, for example, suppression of progression of symptoms, alleviation of symptoms, cure of symptoms, prevention of the occurrence of symptoms, and prevention of recurrence of symptoms. The symptom is, for example, a dysfunction in the oxidative stress disease, and specific examples include motor dysfunction and cognitive impairment. In an embodiment of the present invention, the treatment of the disease can be interchangeably read, for example, as treatment of a disease or treatment of a symptom associated with the disease, and the therapeutic agent can be read, for example, as the therapeutic agent for a disease or the therapeutic agent for a symptom associated with the disease (specific examples include progression inhibitors for symptoms). In an embodiment of the present invention, the pharmaceutical preparation according to an embodiment of the present invention may be used, for example, for any one target or two or more targets with regard to the treatment of the disease or the symptom.

A method of administering a pharmaceutical composition according to an embodiment of the present invention is described as, for example, a method of treating diseases on which edaravone acts directly or indirectly, and a specific example is a method of treating an oxidative stress disease.

The administration of a pharmaceutical composition according to an embodiment of the present invention is not particularly limited except for administering orally or administering intragastrically under the condition 1), 2), or 3) as described above, and for example, reference may be made to administration conditions for the use of an injection containing edaravone. Specifically, when a pharmaceutical composition according to an embodiment of the present invention is used for the treatment of an oxidative stress disease (preferably ALS), reference may be made, for example, to the administration method described in WO 2020/091036 or an administration method using an edaravone injection currently used in clinical practice. Examples of an administration method include daily administration and intermittent administration, specifically, intermittent administration methods used for the treatment of ALS. In other words, a time interval from a consumption of a meal to an administration and a time interval from the administration to a consumption of a next meal may be, for example, time intervals during administration periods of intermittent administration and daily administration. The intermittent administration method is an intermittent administration, that is, for example, a method of administration in which an administration period and an interruption period are combined as one unit, and this unit is repeated two or more times. When an administration period and an interruption period are combined as one unit, and the unit is repeated two or more times, the last period is the interruption period, but the last interruption period may or may not be provided. That is, for example, when the administration period and the interruption period are combined as one unit and the unit is repeated twice, the periods may be combined, for example, as "the administration period, the interruption period, the administration period, and the interruption period" or "the administration period, the interruption period, and the administration period" without providing the last interruption period.

In an embodiment of the present invention, the interruption period is, for example, a period in which the drug is not administered for consecutive several days or more and preferably 7 days or 14 days. The administration period is, for example, for 14 days, and in this case, the drug may be administered for consecutive 14 days or in 10 days in 14 days during the administration period. Here, 10 days in 14 days mean, for example, any 10 days in consecutive 14 days, and 10 days when the drug is administered may be consecutive 10 days or nonconsecutive 10 days divided by one or more periods (e.g., 1 day to 4 days) when the drug is not administered. For the administration period, a preferred period is selected, for example, by observing the patient's condition. More specifically, examples include a method of providing an initial administration period of 14 days, followed by an interruption period of 14 days, and then further repeating an administration period of 10 days in 14 days and an interruption period of 14 days. The number of times of repeating the administration period of 10 days in 14 days and the interruption period of 14 days is not particularly limited and is, for example, one or more times.

A pharmaceutical composition according to an embodiment of the present invention when used for the treatment of an oxidative stress disease (preferably ALS) may be administered to the patient repeatedly, for example, every day or almost every day during the administration period (also referred as "daily administration"). The dose per administration of a pharmaceutical composition according to an embodiment of the present invention is appropriately selected based on, for example, age and status (e.g., severity of the disease) of the patient. The dose of a pharmaceutical composition according to an embodiment of the present invention is determined, for example, as a dose of edaravone contained in the pharmaceutical composition. As a typical specific example, for the dose per administration of the pharmaceutical composition according to an embodiment of the present invention in terms of a dose of edaravone for adults, the lower limit is, for example, 60 mg or 90 mg, the upper limit is, for example, 400 mg, 140 mg, 120 mg, or 105 mg, and the range is, for example, from 60 mg to 400 mg, preferably from 90 to 140 mg, more preferably from 90 to 120 mg, and even more preferably from 90 mg to 105 mg, and the dose is particularly preferably 90 mg, 100 mg, 105 mg, or 120 mg, and in particular, preferably 100 mg or 105 mg, and most preferably 105 mg.

In addition, when a pharmaceutical composition according to an embodiment of the present invention is used for the treatment of an oxidative stress disease (preferably ALS), for example, the dose per administration during the administration period of an intermittent administration method is the same as the dose described above.

For edaravone injection, sold under the brand name "Radicut" (trade name) in Japan, which is currently used as a therapeutic agent for ALS in a clinical setting, the dose per administration thereof is set to 60 mg as edaravone. For a pharmaceutical composition according to an embodiment of the present invention, which is for oral administration or intragastric administration, to attain the same effect as in the intravenous injection of the edaravone injection at 60 mg per administration, the dose of the subject pharmaceutical composition is preferably, for example, set to 90 to 105 mg as edaravone, and more specifically, it is preferably set to 105 mg as edaravone per administration.

An administration frequency of the pharmaceutical composition according to an embodiment of the present invention is not particularly limited whether, for example, it is for oral administration or for intragastric administration, and the administration frequency is not particularly limited whether it is for everyday administration or for intermittent administration. The administration frequency is selected to a preferred frequency, for example, by observing the patient's condition. As a specific example, the number of times of administration is preferably once or twice per day and more preferably once per day in consideration of, for example, the burden of patients.

EXAMPLES

Next, the present invention will be described with reference to examples and study examples, but the present invention is not limited to these. Hereinafter, an edaravone oral formulation was used as the pharmaceutical composition according to an embodiment of the present invention, and evaluation using oral administration or intragastric administration via a tube was carried out. The edaravone oral formulation may also be referred to as the edaravone intragastric formulation when used for intragastric administration.

Example 1: Effects of Meal Consumption Before Administration of Edaravone Oral Formulation on Pharmacokinetics of Edaravone Effects of meal consumption before administration of the edaravone oral formulation on the pharmacokinetics of edaravone were evaluated. Specifically, clinical studies #1, #2, and #3 described below were conducted on separate days in Japanese healthy adult male subjects. In each of clinical studies #1, #2, and #3, one dose each of edaravone oral formulations (edaravone suspensions) of formulas #1, #2, and #3 shown in Table 1 below were used respectively and administered orally once during the study period. In addition, the number of subjects in each clinical study is shown in Table 2 described below. For each clinical study, a reference study was conducted (reference example), in which the edaravone oral formulation was administered in fasted conditions as described below, and in each clinical study and the corresponding reference study, the edaravone oral formulation was each administered to the same subjects.

TABLE 1

| Formulas used in clinical studies #1, #2, and #3 | | | |
|---|---|---|---|
| | Study #1 amount | Study #2 amount | Study #3 amount |
| Edaravone | 200 mg | 100 mg | 105 mg |
| Polyvinyl alcohol | 10 mg | 5 mg | 5 mg |
| Xanthan gum | | 15 mg | 15 mg |
| Sodium hydrogen sulfite | | 5 mg | 5 mg |
| L-Cysteine hydrochloride hydrate | | 2.5 mg | 2.5 mg |
| Sodium hydroxide | | q.s. | q.s. |
| Phosphoric acid | | q.s. | q.s. |
| Simethicone emulsion | | 2.5 mg | 2.5 mg |
| D-Sorbitol | | 2000 mg | 2000 mg |
| Purified water | q.s. | q.s. | q.s. |
| Total | 10 mL | 5 mL | 5 mL |

For the high-fat meal, a meal with total calories per meal of 800 to 1000 kilocalories and calorie intake from lipid of 50% was used. For the standard meal, a meal with total calories per meal of 400 to 500 kilocalories and calorie intake from lipid of 25% was used. For the light meal, a liquid-type nutritional supplement with total calories per meal of 250 kilocalories (enteral nutritional supplement: Ensure Liquid (trade name)) was used.

Clinical Study #1: Comparative Example for First Time Interval Condition 1)

The edaravone oral formulation (formula #1) was administered orally to the subjects 30 minutes after high-fat meal consumption. Blood samples were each collected before the administration, and 15 minutes, 30 minutes, 1 hour, 1.5 hours, 2 hours, 4 hours, 6 hours, 8 hours, 12 hours, 24 hours, 36 hours, and 48 hours after the administration, and the concentrations of unchanged edaravone in plasma were measured. On the other hand, as a reference example, the edaravone oral formulation was administered orally to the same subjects in fasted conditions, blood samples were collected, and the concentrations of unchanged edaravone in plasma were measured in the same manner. For the administration in fasted conditions, the edaravone oral formulation was administered orally after a lapse of 10 hours or more from the previous meal consumption (the same applies hereinafter). None of the subjects consumed a next meal until the blood sample collection 4 hours after the administration was completed. The resulting PK profiles are shown in Table 2 below.

Clinical Study #2: Comparative Example for First Time Interval Condition 1)

The edaravone oral formulation (formula #2) was administered orally to the subjects 4 hours after high-fat meal consumption. Blood samples were each collected before the administration, and 5 minutes, 15 minutes, 30 minutes, 1 hour, 1.5 hours, 2 hours, 4 hours, 6 hours, 8 hours, 12 hours, 24 hours, 36 hours, and 48 hours after the administration, and the concentrations of unchanged edaravone in plasma were measured. On the other hand, as a reference example, the edaravone oral formulation was administered orally to the same subjects in fasted conditions, blood samples were collected, and the concentrations of unchanged edaravone in plasma were measured in the same manner. For the administration in fasted conditions, the edaravone oral formulation was administered orally after a lapse of 10 hours or longer from the previous meal consumption. None of the subjects consumed a next meal until the blood sample collection 4 hours after the administration was completed. The resulting PK profiles are shown in Table 2 below.

Clinical Study #3: Examples for First Time Interval Conditions 1), 2), and 3), and Comparative Example for Time Interval Condition 2)

As examples, the edaravone oral formulation (formula #3) was administered orally to each subject of 8 hours after high-fat meal consumption, 4 hours after standard meal consumption, and 2 hours after light meal consumption. Blood samples were each collected before the administration, and 5 minutes, 15 minutes, 30 minutes, 45 minutes, 1 hour, 1.5 hours, 2 hours, 4 hours, 6 hours, 8 hours, 10 hours, 12 hours, 24 hours, 36 hours, and 48 hours after the administration, and the concentrations of unchanged edaravone in plasma were measured. In addition, as a comparative example, the edaravone oral formulation was administered orally to the same subjects 2 hours after standard meal consumption, blood samples were collected, and the concentrations of unchanged edaravone in plasma were measured in the same manner. On the other hand, as a reference example, the edaravone oral formulation was administered orally to the same subjects in fasted conditions, blood samples were collected, and the concentrations of unchanged edaravone in plasma were measured in the same manner. For the administration in fasted conditions, the edaravone oral formulation was administered orally after a lapse of 10 hours or longer from the previous meal consumption. None of the subjects consumed a next meal until the blood sample collection 4 hours after the administration was completed. The resulting PK parameters are shown in Table 2 below.

For the effects of high-fat meal consumption, the following results were obtained. First, a comparison was made between the comparative example of #2 (#2: 4 h after high-fat meal) in which the edaravone oral formulation was administered 4 hours after high-fat meal consumption and the example of #3 (#3: 8 h after high-fat meal) in which the edaravone oral formulation was administered 8 hours after high-fat meal consumption. As shown in Table 2 above, in the comparative example of #2 (#2: 4 h after high-fat meal), as a result of the administration 4 hours after high-fat meal consumption, a decrease in the Cmax by 44% (percentage of decrease, the same applies hereinafter) and a decrease in the AUC by 24% were observed in comparison with the administration in fasted conditions (#2: Fasted). In contrast to this, as shown in Table 2, in the example of the study #3 (#3: 8 h after high-fat meal), with the administration 8 hours after high-fat meal consumption satisfying the first time interval condition 1) described above, no decrease in the Cmax and AUC was observed in comparison with the administration in fasted conditions (#3: Fasted). The formulas of the edaravone oral formulations used in the comparative example of #2 and the example of #3 are almost identical, and thus, an embodiment of the present invention was found to be able to maintain the pharmacokinetics of edaravone in a manner similar to the administration in fasted conditions by the timing of administration after meal consumption. In addition, in the comparative example of #1 (#1: 30 min after high-fat meal), the time from meal consumption to the administration of the edaravone oral formulation was further shortened to 30 minutes after high-fat meal consumption.

As a result, a decrease in the Cmax by 82% and a decrease in the AUC by 61% were observed in comparison with the administration in fasted conditions (#1: Fasted), and the

TABLE 2

PK parameters of edaravone due to meal consumption before administration of edaravone oral formulation

| Study | Meal condition | Edaravone dose (mg) | Statistics | $t_{max}$ (h) | $C_{max}$ (ng/mL) | $AUC_{0-\infty}$ (ng · h/mL) | $t_{1/2}$ (h) |
|---|---|---|---|---|---|---|---|
| Study #1 (n = 6) | Fasted | 200 | Mean | 0.42 | 4933 | 6312.88 | 9.05 |
| | | | SD | 0.13 | 1268 | 1246.42 | 2.37 |
| Study #1 (comparative example) (n = 5) | 30 min after high-fat meal | 200 | Mean | 1.35 | 899 (82%↓) | 2466.38 (61%↓) | 5.23 |
| | | | SD | 1.56 | 463.9 | 824.73 | 1.71 |
| Study #2 (n = 9) | Fasted | 100 | Mean | 0.36 | 1810 | 1646.73 | 9.33 |
| | | | SD | 0.25 | 849.8 | 432.96 | 4.87 |
| Study #2 (comparative example) (n = 9) | 4 h after high-fat meal | 100 | Mean | 0.47 | 1012 (44% ↓) | 1247.4 (24%↓) | 7.66 |
| | | | SD | 0.32 | 603.3 | 425.22 | 4.12 |
| Study #3 (n = 16) | Fasted | 105 | Mean | 0.38 | 2318 | 2165 | 8.17 |
| | | | SD | 0.13 | 1229 | 673 | 2.29 |
| Study #3 (example) (n = 16) | 8 h after high-fat meal | 105 | Mean | 0.36 | 2525 (→) | 2209 (→) | 7.38 |
| | | | SD | 0.19 | 1337 | 658 | 1.97 |
| Study #3 (example) (n = 16) | 4 h after standard meal | 105 | Mean | 0.44 | 2020 (→) | 2073 (→) | 9.05 |
| | | | SD | 0.19 | 1114 | 641 | 5.07 |
| Study #3 (example) (n = 16) | 2 h after light meal | 105 | Mean | 0.41 | 1898 (→) | 1955 (→) | 7.31 |
| | | | SD | 0.2 | 865.9 | 523 | 4.3 |
| Study #3 (comparative example) (n = 16) | 2 h after standard meal | 105 | Mean | 0.63 | 1276 (%↓) | 1717 (21%↓) | 11.25 |
| | | | SD | 0.32 | 805.6 | 463 | 8.35 | percentages of the decreases were greater than those in the comparative example of #2. The content of edaravone in the edaravone oral formulation of the formula #1 used in the comparative example of #1 was about twice those in the edaravone oral formulations used in the comparative example of #2 and the example of #3. This revealed that the effect of the present invention is not compensated, for example, by the increased edaravone content in the edaravone oral formulation but is obtained by the first time interval from meal consumption to the administration of the edaravone oral formulation according to the type of meal.

For the effects of the standard meal consumption and light meal consumption, the following results were obtained. That is, as shown in Table 2 above, both in the example of the study #3 (#3: 4-h after standard meal) with the administration 4 hours after the standard meal consumption satisfying the first time interval condition 2) and in the example of the study #3 (#3: 2-h after standard meal) with the administration 2 hours after the light meal consumption satisfying the first time interval condition 3), no decrease in the Cmax and AUC was observed in comparison with the administration in fasted conditions (#3: Fasted). No decrease in the Cmax and AUC was thus observed in the example of the study #3 above, and this was also supported by results of an analysis of variance shown below.

That is, from the results of the edaravone PK parameters, an analysis of variance was conducted on the AUC and Cmax in consideration of the meal condition. This result is shown in Table 3 below. In addition, results of summary statistics for the Cmax are shown in Table 4 below, and spaghetti plots are shown in FIG. 1. The spaghetti plots in FIG. 1 show results from individual subjects, in which results from the same subjects are connected with lines between results in the administration in fasted conditions and results in the postprandial administration.

TABLE 3

Ratios of PK parameters determined by analysis of variance and 90% confidence intervals

| Parameter (Unit) | Meal condition | Least-square mean | Ratio [90% Confidence interval] (dose with meal/fasted) |
|---|---|---|---|
| $C_{max}$ (ng/mL) | Fasted | 2024 | — |
| | 8 hours after high-fat meal | 2192 | 1.083 [0.821-1.429] |
| | 4 hours after standard meal | 1764 | 0.872 [0.661-1.150] |
| | 2 hours after light meal | 1659 | 0.820 [0.621-1.082] |
| $AUC_{0-\infty}$ (ng · h/mL) | Fasted | 2072 | — |
| | 8 hours after high-fat meal | 2123 | 1.025 [0.931-1.128] |
| | 4 hours after standard meal | 1987 | 0.959 [0.871-1.056] |
| | 2 hours after light meal | 1885 | 0.910 [0.827-1.002] |

TABLE 4

Summary statistics for Cmax

| Meal condition | Mean | SD | CV % | Min | Median | Max |
|---|---|---|---|---|---|---|
| Fasted | 2318 | 1229 | 53 | 797 | 1992 | 4816 |
| 8 hours after high-fat meal | 2525 | 1337 | 52.9 | 595 | 2237 | 5270 |
| 4 hours after standard meal | 2020 | 1114 | 55.2 | 642 | 1736 | 4286 |
| 2 hours after light meal | 1898 | 866 | 45.6 | 388 | 1957 | 3237 |

As shown in Table 3 above, the analysis of variance indicated that for the least squares mean ratio of the AUC of the example administered under each first time interval condition after the meal consumption to the AUC of the reference example administered in fasted conditions (Fasted), the 90% confidence interval was in the range of 0.8 to 1.25, which is a common criterion for equivalence. This result indicates that the edaravone oral formulation administered 8 hours after high-fat meal consumption, 4 hours after standard meal consumption, and 2 hours after light meal consumption can exert an effect of maintaining the pharmacokinetics similar to those in the administration in fasted conditions without effects of meals on the AUC. In addition, as shown in Table 3 above, for the Cmax, although the 90% confidence intervals of the ratio (numerical values in parentheses in the column of the ratio) did not fall within the range of 0.8 to 1.25, which is the above criterion, because of large coefficients of variation (ratios of SD to the mean value), the point estimates of the ratio (the value outside the parentheses in the Confidence column) indicated no significant change and were within the range of the above criterion. Furthermore, as shown in the summary statistics of the Cmax in Table 4 above and the spaghetti plots in FIG. 1, the administration in fasted conditions and the postprandial administration resulted in values of each subject distributed in the range of about 1000 to about 5000 with a median of about 2000 in a similar manner regardless of the conditions of each postprandial administration, showing no change in comparison with the administration in fasted conditions.

The example of the study #3 thus indicated that administering the edaravone oral formulation 8 hours after high-fat meal consumption satisfying the condition 1), 4 hours after standard meal consumption satisfying the condition 2), and 2 hours after light meal consumption satisfying the condition 3) can achieve the Cmax and AUC similar to those in the oral administration in fasted conditions and can avoid effects of the meal on the pharmacokinetics of edaravone.

As described above, the examples confirmed that administering after meal consumption in the timing of the first time interval conditions 1), 2), and 3) can maintain pharmacokinetics similar to those in administering the same edaravone oral formulation in fasted conditions. In addition, these results supported that the pharmaceutical composition according to an embodiment of the present invention is any composition containing edaravone as an active ingredient, the composition itself is not particularly limited, and even in using the pharmaceutical composition of the same composition, the effect of the present invention can be obtained by setting conditions for administration as described above according to the types of meals.

Example 2: Effects of Meal Consumption after Administration of Edaravone Oral Formulation on Pharmacokinetics of Edaravone 1

Effects of meal consumption 1 hour after administration of the edaravone oral formulation on the pharmacokinetics of edaravone were evaluated. Specifically, a clinical study #4 described below was conducted on the same subjects in Japanese healthy adult male subjects. In the clinical study #4, the edaravone oral formulation of the formula #2 in Table 1 above was used and administered orally once during the study period. In addition, the same high-fat meal as that used in Example 1 above was used.

Clinical Study #4

As a post-administration consumption group, the same subjects in fasted conditions after a lapse of 10 hours or longer from meal consumption were orally administered with the edaravone oral formulation, and the high-fat meal was consumed 1 hour after the administration. Blood samples were each collected before the administration, and 5 minutes, 15 minutes, 30 minutes, 1 hour, 1.5 hours, 2 hours, 4 hours, 6 hours, 8 hours, 12 hours, 24 hours, 36 hours, and 48 hours after the administration, and the concentrations of unchanged edaravone in plasma were measured. The consumption of the high-fat meal 1 hour after the administration was carried out after the blood sample collection 1 hour after the administration, and a subsequent meal was not consumed until the blood sample collection 4 hours after the administration was completed. On the other hand, as a fasted group for reference, the edaravone oral formulation was administered orally to the same subjects in fasted conditions, blood samples were collected, and the concentrations of unchanged edaravone in plasma were measured in the same manner. The subjects in the fasted group did not consume a meal either until the blood sample collection 4 hours after the administration was completed. The resulting PK parameters are shown in Table 5 below.

TABLE 5

PK parameters of edaravone due to meal consumption after administration of edaravone oral formulation

| Study | Meal condition | Edaravone dose (mg) | Statistics | $t_{max}$ (h) | $C_{max}$ (ng/mL) | $AUC_{0-\infty}$ (ng · h/mL) | $t_{1/2}$ (h) |
|---|---|---|---|---|---|---|---|
| Study #4 (n = 9) | Fasted | 100 | Mean | 0.36 | 1810 | 1646.73 | 9.33 |
|  |  |  | SD | 0.25 | 849.8 | 432.96 | 4.87 |
| Study #4 (n = 9) | 1 h before high-fat meal | 100 | Mean | 0.6 | 1502 (→) | 1475.31 (→) | 9.65 |
|  |  |  | SD | 0.44 | 1272 | 658.1 | 5.41 |

A comparison was made between the post-administration consumption group, in which the high-fat meal was consumed 1 hour after the administration of the edaravone oral formulation, and the fasted group, in which no meal was consumed for another 4 hours or longer after the administration in fasted conditions. As a result, as shown in Table 5 above, the post-administration consumption group showed only a slight decrease in the Cmax by about 17.0% and the AUC by about 10.4% in comparison with the fasted group, and no significant difference was observed. Thus, the meal consumption 1 hour after the oral administration was found to have no effect on the pharmacokinetics of edaravone.

Figure 2:
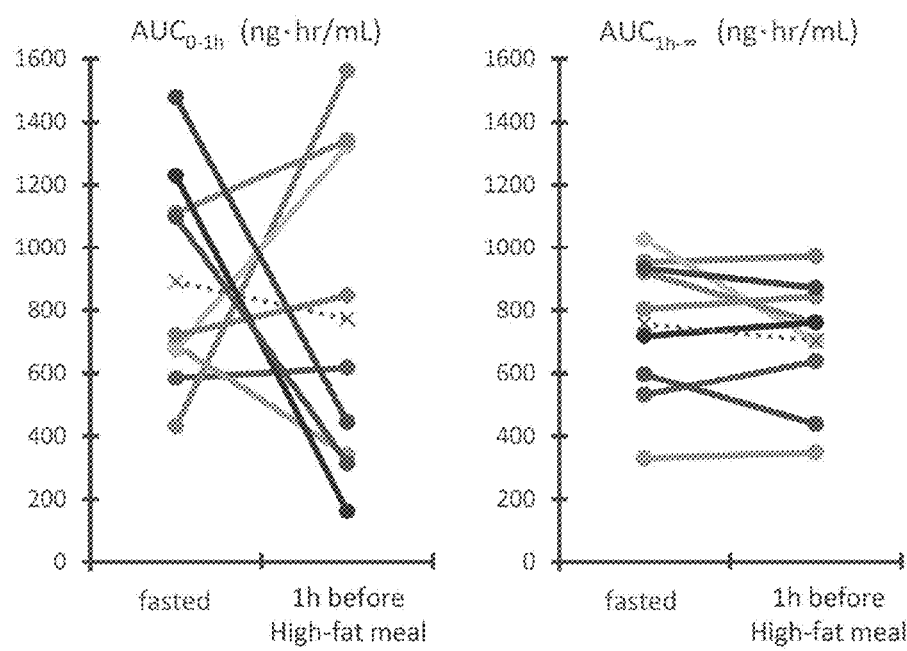
FIG. 2 shows spaghetti plots comparing the $AUC_{0-1\ h}$ and $AUC_{1\ h-\infty}$ after oral administration of an edaravone oral formulation between a high-fat meal group consuming a high-fat meal 1 hour after the administration and a fasted group administered under fasted conditions (The circles with solid lines represent individual values, and the crosses with dotted lines represent mean values)

In addition, the $AUC_{0-\infty}$ after the administration of the edaravone oral formulation was evaluated separately on the results from 0 hour to 1 hour after the administration (0 to 1 h, before the consumption of a meal resumed after the administration) ($AUC_{0-1\,h}$) and the results 1 hour after the administration (1 h to ∞ h, after the consumption of a meal resumed after the administration) ($AUC_{1\,h-\infty}$) for the post-administration consumption group (1 h before high-fat meal) and the fasted group (Fasted). These results are shown in Table 6 below and spaghetti plots in FIG. 2. As shown in Table 6 below and FIG. 2, in the post-administration consumption group (1 h before high-fat meal), although a slight decrease in the $AUC_{0-1\,h}$ occurred from the edaravone administration to 1 hour before the consumption of a meal resumed after the administration in comparison with the administration in the fasted group (Fasted), no change in the $AUC_{1\,h-\infty}$ was noted 1 hour and longer after the edaravone administration. From this, the result of the slight decrease in the $AUC_{0-1\,h}$ in the post-administration consumption group is not considered due to decreases in the Cmax and AUC due to effects of the meal but is considered to be a result due to fluctuations in the same subjects (i.e., day-to-day fluctuations due to acquiring the data of fasted conditions and the meal consumption from the same subjects on separate days).

TABLE 6

AUC of edaravone when high-fat meal is consumed 1 hour after administration of edaravone oral formulation

|  | Meal condition | $AUC_{0-1\,h}$ (ng · h/mL) | $AUC_{1\,h-\infty}$ (ng · h/mL) |
|---|---|---|---|
| Study #4 (n = 9) | Fasted | 890 ± 349 | 756 ± 232 |
| Study #4 (n = 9) | 1 h before high-fat meal | 772 ± 519 | 703 ± 202 |

The above results indicated that when the high-fat meal was consumed 1 hour after the administration of the edaravone oral formulation, no change in the pharmacokinetics of edaravone was noted in comparison with the administration in fasted conditions, and thus a meal after the administration has no effect on the pharmacokinetics. The results of the evaluation using the high-fat meal thus indicated no effect on the pharmacokinetics of edaravone. Thus, regardless of the high-fat meal, consumption of the standard meal and the light meal 1 hour after the administration of the edaravone oral formulation is considered to cause no change in the pharmacokinetics of edaravone in comparison with the administration in fasted conditions, and the meal is considered to have no effect on the pharmacokinetics.

Example 3: Evaluation of Edaravone in Caco-2 Cell Membrane Permeability Test

Caco-2 cells were seeded on a 24-well plate, cultured at 37° C. for 21 to 23 days in a $CO_2$ incubator, and then a Caco-2 cell monolayer membrane permeability test was conducted. After checking the membrane resistance value of the cell layer after the culture, the culture medium in the plate was replaced with HBSS (pH 7.4). After preincubation at 37° C. for 1 hour, edaravone and control compounds at predetermined concentrations were each added to the apical side and incubated at 37° C. for 2 hours. For the control compounds, [$^3$H]propranolol as a high membrane permeability control and [$^{14}$C]mannitol as a low membrane permeability control were used. Then, the concentrations of edaravone and the control compounds on the basal side were each measured, and the permeability coefficients ($P_{app}$) were calculated.

These results are shown in Table 7 below. The data of $P_{app}$ are indicated by mean±SD. As shown in Table 7 below, edaravone exhibited membrane permeability equal to or higher than that of propranolol used as the high membrane permeability control compound.

TABLE 7

Permeability coefficient of edaravone

| Compound | Concentration (μmol/L) | $P_{app}$ (×10$^{-6}$ cm/sec) Apical to basal (n = 3) |
|---|---|---|
| Edaravone | 100 | 32.0 ± 1.7 |
| [$^3$H]Propranolol | 10 | 28.9 ± 1.1 |
| [$^{14}$C]Mannitol | 10 | 0.530 ± 0.007 |

Cell membrane permeability is known to be constant regardless of the concentration of the substance when no transporter is involved. The control compounds, propranolol and mannitol, are not substrates for transporters P-gp and BCRP expressed in Caco-2 cells, and thus the values of the permeability coefficient are not considered to change depending on the concentrations used in the test. Thus, further, the following study was conducted to confirm that edaravone is not a substrate for transporters P-gp and BCRP as well.

That is, Caco-2 cells were seeded on a 96-well plate, cultured at 37° C. for 10 to 11 days in a $CO_2$ incubator, and then a transcellular transport study was conducted. Then, a ratio of $P_{app}$ from the apical side to the basal side to $P_{app}$ from the basal side to the apical side was calculated. The efflux ratio was calculated as the ratio of the mean values of $P_{app}$ calculated from three measurements. This result is shown in Table 8 below. As shown in Table 8 below, the efflux ratio of edaravone did not exceed 2 and was not affected by addition of typical inhibitors of P-gp and/or BCRP. Thus, this indicated that edaravone is not a substrate for P-gp and BCRP.

TABLE 8

Ratios of permeability coefficient of edaravone in Caco-2 cells in both directions in presence or absence of typical inhibitors of P-gp and BCRP

| Compound (Added concentration) | Inhibitor (Added concentration) | Efflux ratio |
|---|---|---|
| Edaravone (10 μmol/L) | — | 0.9 |
| | Quinidine (30 μmol/L) | 1 |
| | Novobiocin (30 μmol/L) | 0.8 |
| | Quinidine (30 μmol/L) + Novobiocin (30 μmol/L) | 0.6 |

Quinidine: P-gp inhibitor
Novobiocin: BCRP inhibitor

Literatures by Sun et al. (Pharmaceutical Research, Vol. 19, No. 10, 2002) and Yamashita et al. (European Journal of Pharmaceutical Sciences 10 (2000) 195-204) indicate that the permeability coefficient of a drug by the Caco-2 cell membrane permeability test correlates with the absorption rate of the drug in humans. In addition, literatures by Paterson et al. (Pharmacologia Cliniea 2, 127-133 (1970)) and Borgstrom et al. (Journal of Pharmacokinetics and Biopharmaceutics, VoL 9 No. 4, 1981) indicate that when administered orally to humans, almost all of propranolol is absorbed in the intestine.

As described above, edaravone exhibited a permeability coefficient equal to or higher than that of propranolol. Thus, edaravone when administered orally to humans was considered to exhibit high absorption rate and was found to be classified as a high permeability compound. The report by Wu et al. (Non-Patent Document 1) describes that high permeability compounds are less susceptible to effects of a meal on pharmacokinetics as described above. On the contrary, however, despite the fact that edaravone has a high permeability, its pharmacokinetics was affected by a meal as also described in Examples 1 and 2 above. The pharmacokinetics of edaravone is thus affected by a meal; further, the effect varies with the type of meal; and the effect on the pharmacokinetics is avoided by setting the timing of administration to the conditions 1), 2), and 3) described above according to the type of meal. These have been found by the present inventors for the first time.

Example 4: Pharmacokinetics of Edaravone in ALS Patients

To evaluate the pharmacokinetics of edaravone in ALS patients, a clinical study #5 shown below was conducted in ALS patients who can live daily life independently (the patient group).

Clinical Study #5

The edaravone oral formulation was administered orally to the patient group in fasted conditions after a lapse of 10 hours or longer from consumption of a meal. In the patient group, ALS patients who had been already administered with an edaravone intravenous infusion formulation were orally administered with the edaravone oral formulation after a lapse of 48 hours or longer from the time of completion of the previous administration of the intravenous infusion formulation. The same edaravone oral formulation as the formula #3 in Table 1 above was used. Then, blood samples were each collected before the administration, and 5 minutes, 15 minutes, 30 minutes, 45 minutes, 1 hour, 1.5 hours, 2 hours, 4 hours, 6 hours, 8 hours, 10 hours, 12 hours, and 24 hours after the administration, and the concentrations of unchanged edaravone in plasma were measured. The patient group did not consume a meal after the administration until the blood sample collection 4 hours after the administration was completed.

Clinical Study #9

On the other hand, a clinical study #9 shown below was conducted in healthy adult male and female subjects (42 in total) (the reference group). That is, the edaravone oral formulation of the formula #3 was administered orally to the reference group in fasted conditions after a lapse of 10 hours or longer. Then, blood samples were each collected before the administration, and 5 minutes, 15 minutes, 30 minutes, 45 minutes, 1 hour, 1.5 hours, 2 hours, 4 hours, 6 hours, 8 hours, 10 hours, 12 hours, 24 hours, 36 hours, and 48 hours after the administration, and the concentrations of unchanged edaravone in plasma were measured. The reference group did not consume a meal after the administration either until the blood sample collection 4 hours after the administration was completed.

Figure 3:
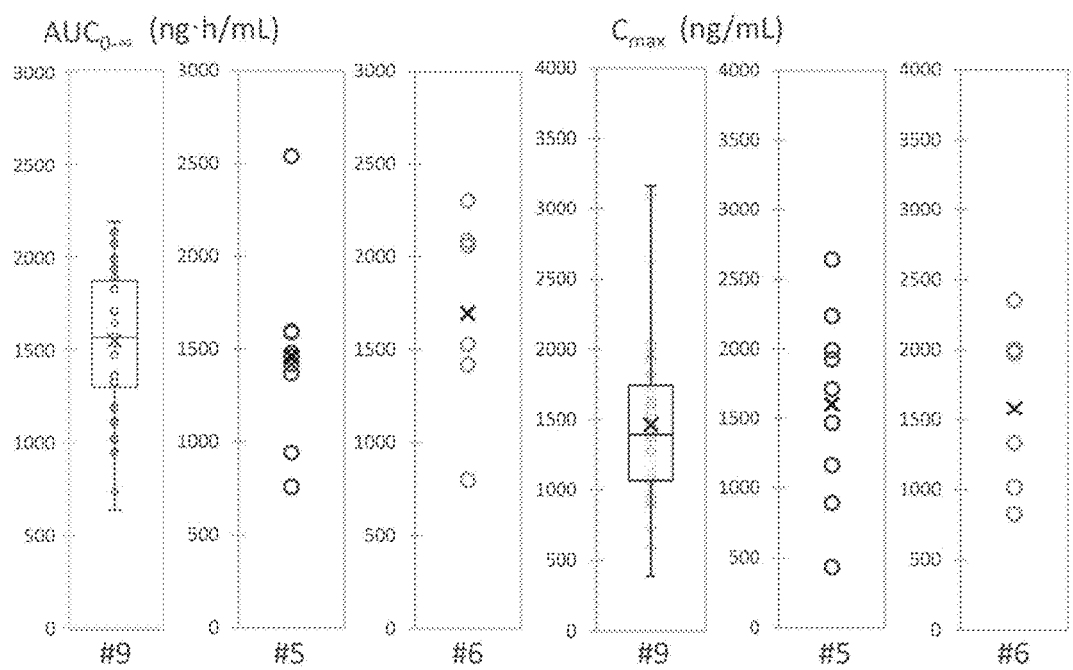
FIG. 3 shows a box plot (study #9) and individual plots (studies #5, #6, and #9) for the $AUC_{0-\infty}$ and Cmax after administration of an edaravone oral formulation (The circles represent individual values, and the crosses represent mean values. In the box plot, the top and bottom of the whiskers represent the maximum and minimum values, and the upper limit, middle, and lower limit of the box represent the 25th, 50th, and 75th percentile values, respectively)

The resulting PK parameters were corrected for body weight of each subject adjusted to 70 kg by a proportional calculation for each of the patient group and the reference group. The results of the PK parameters before correction of the patient group and the reference group are shown in Table 9 below. In addition, the results of the PK parameters after correction of the patient group are shown as box-whisker plots of #9 (the reference group), and individual plots of #5 (the patient group) and #9 (the reference group) in FIG. 3. In FIG. 3, X represents a mean value. As shown in Table 9 below, the difference in the Cmax before weight correction was 15%, and the difference in the AUC before weight correction was 1.5% between the patient group and the reference group, but as shown in FIG. 3, the difference in the Cmax after weight correction was 9.8%, and the difference in the AUC after weight correction was 5.8%, both being within 10%. On the other hand, the mean value±standard error of the Cmax after weight correction of the patient group was 1607±231, and the mean value±standard error of the AUC after weight correction of the patient group was 1461±166, both with a large standard error. Thus, the difference in the Cmax and the difference in the AUC before weight correction between the patient group and the reference group seen in Table 9 below are considered due to the difference in body weight between the patient group and the reference group, and the difference in the Cmax and the difference in the AUC after weight correction between the patient group and the reference group observed in FIG. 3 are each considered to be within the range of error.

TABLE 9

PK Parameters of edaravone in ALS patients

| subjects | Edaravone dose (mg) | Statistics | $t_{max}$ (h) | $AUC_{inf}$ (ng · h/mL) | $C_{max}$ (ng/mL) |
|---|---|---|---|---|---|
| healthy | 105 | Mean | 0.44 | 1762 | 1656 |
| (n = 42) |  | SD | 0.17 | 540 | 734 |
| ALS patients | 105 | Mean | 0.31 | 1736 | 1903 |
| (n = 9) |  | SD | 0.15 | 811 | 978 |

As described above, the result of comparing the Cmax and AUC of edaravone after the administration of the edaravone oral formulation between ALS patients and healthy adults revealed that the pharmacokinetics of edaravone is similar between ALS patients and healthy adults and that sufficient plasma concentration of edaravone is maintained in ALS patients as well as in healthy adults. From this, it can be said that oral administration of edaravone itself does not affect the plasma concentration regardless of whether the subject is a patient.

Example 5: Pharmacokinetics of Edaravone in Administration Via Percutaneous Endoscopic Gastrostomy Tube (PEG Tube)

Pharmacokinetics of edaravone in administration of the edaravone oral formulation via a PEG tube was evaluated. Specifically, a clinical study #6 described below was conducted in ALS patients with a percutaneous endoscopic gastrostomy tube (PEG tube) (the patient group). In the clinical study #6, the edaravone oral formulation of the formula #3 shown in Table 1 was used.
Clinical Study #6

The edaravone oral formulation was administered via a PEG tube to the patient group in fasted conditions after a lapse of 10 hours or longer from consumption of a meal. That is, first, 100 mL of lukewarm water was injected through a PEG tube 1 hour before the administration of the edaravone oral formulation, and 10 mL of lukewarm water was injected through a PEG tube immediately before the administration. Then, the edaravone oral formulation was administered to the PEG tube, and further 10 mL of water was injected through the PEG tube three times to wash in the edaravone oral formulation. In the patient group, ALS patients who had been already administered with an edaravone intravenous infusion formulation were administered with the edaravone oral formulation via a PEG tube after a lapse of 48 hours or longer from the time of completion of the previous administration of the intravenous infusion formulation. Blood samples were each collected before the administration, and 15 minutes, 30 minutes, 1 hour, 2 hours, 4 hours, 8 hours, and 24 hours after the administration, and the concentrations of unchanged edaravone in plasma were measured. The patient group did not consume a meal until the blood sample collection 4 hours after the administration via a PEG tube was completed. For the reference example, the results of the reference group in Example 4, in which the edaravone oral formulation of the same formula #3 was administered orally and blood samples were collected, were utilized.

The resulting PK parameters were corrected for body weight of each subject in the patient group adjusted to 70 kg by a proportional calculation. The results of the PK parameters before correction of the patient group are shown in Table 10 below. In addition, the results of the PK parameters after correction of the patient group are shown in individual plots as #6 in FIG. 3. A comparison was made between the patient group administered via a PEG tube in Table 10 below and the reference group administered orally in Table 9 above. As a result, a difference in the Cmax before weight correction of 30% and a difference in the AUC before weight correction of 33% were observed between the patient group administered via a PEG tube and the reference group administered orally, but as shown in FIG. 3, the difference in the Cmax after weight correction was 8.3%, and the difference in the AUC after weight correction was 9.5%, both being within 10%. On the other hand, as shown in FIG. 3, the mean value±standard error of the Cmax after weight correction of the patient group administered via a PEG tube was 1585±251, and the mean value±standard error of the AUC after weight correction of the patient group was 1698±228, both with a large standard error. Thus, the difference in the Cmax and the difference in the AUC before weight correction between the patient group administered via a PEG tube and the reference group administered orally seen in Table 10 below are considered due to the difference in body weight between the patient group administered via a PEG tube and the reference group administered orally, and the difference in the Cmax and the difference in the AUC after weight correction between the patient group administered via a PEG tube and the reference group administered orally seen in FIG. 3 are each considered to be within the range of error.

TABLE 10

PK Parameters of edaravone in ALS patients in administration via a PEG-tube

| Edaravone dose (mg) | Statistics | $t_{max}$ (h) | $AUC_{inf}$ (ng · h/mL) | $C_{max}$ (ng/mL) |
|---|---|---|---|---|
| 105 | Mean | 0.33 | 2344 | 2163 |
|  | SD | 0.13 | 971 | 902 |

The results of the oral administration in Example 4 above and the results of the administration via a PEG tube in this Example 5 indicated that the Cmax and AUC of edaravone after administration of the edaravone oral formulation via a PEG tube were similar to the results after the oral administration of the same edaravone oral formulation. This suggests no difference in the pharmacokinetics of edaravone between administration via a PEG tube and oral administration and revealed that sufficient plasma concentration of edaravone is maintained in administration via a PEG tube as well as in oral administration.

Example 6: Dose of Edaravone in Oral Formulation Exhibiting Bioavailability Equivalent to that of Edaravone Intravenous Administration The dose of edaravone in the oral formulation exhibiting bioavailability equivalent to that of the 60-mg edaravone intravenous (IV) administration was investigated. Specifically, clinical studies #7 and #8 described below were conducted in healthy adult male subjects for each subject group. In clinical studies #7 and #8, one dose each of edaravone oral formulations (edaravone suspensions) of formulas #7 and #8 shown in Table 11 below were used respectively and administered orally once during the study period.

TABLE 11

Formulas used in studies #7 and #8

| | Study #7 amount | | | | | Study #8 amount |
|---|---|---|---|---|---|---|
| Edaravone | 30 mg | 60 mg | 120 mg | 200 mg | 300 mg | 100 mg |
| Polyvinyl alcohol | 50 mg | 50 mg | 10 mg | 10 mg | 10 mg | 5 mg |
| Xanthan gum | | | | | | 15 mg |
| Sodium hydrogen sulfite | | | | | | 5 mg |
| L-Cysteine hydrochloride hydrate | | | | | | 2.5 mg |
| Sodium hydroxide | | | | | | q.s. |
| Phosphoric acid | | | | | | q.s. |
| Simethicone emulsion | | | | | | 2.5 mg |
| D-Sorbitol | | | | | | 2000 mg |
| Purified water | q.s. | q.s. | q.s. | q.s. | q.s. | q.s. |
| Total | 50 mL | 50 mL | 10 mL | 10 mL | 10 mL | 5 mL |

Clinical Study #7

Any of the edaravone oral formulations (formula #7) with an edaravone content of 30 mg, 60 mg, 120 mg, 200 mg, or 300 mg was administered orally to subjects in fasted conditions after a lapse of 10 hours or longer from consumption of a meal. The edaravone oral formulations with each content were each administered orally to 6 subjects. Blood samples were each collected before the administration, and 15 minutes, 30 minutes, 1 hour, 1.5 hours, 2 hours, 4 hours, 6 hours, 8 hours, 12 hours, 24 hours, 36 hours, and 48 hours after the administration, the concentrations of unchanged edaravone were measured, and the AUCs were calculated. The subjects did not consume a meal after the administration until the blood sample collection 4 hours after the administration was completed.

Clinical Study #8

The edaravone oral formulations (formula #8) with an edaravone content of 100 mg was administered orally to 9 subjects in fasted conditions after a lapse of 10 hours or longer from consumption of a meal. Blood samples were each collected before the administration, and 5 minutes, 15 minutes, 30 minutes, 1 hour, 1.5 hours, 2 hours, 4 hours, 6 hours, 8 hours, 12 hours, 24 hours, 36 hours, and 48 hours after the administration, the concentrations of unchanged edaravone in plasma were measured, and the AUCs were calculated. The subjects did not consume a meal after the administration either until the blood sample collection 4 hours after the administration was completed.

Figure 4:
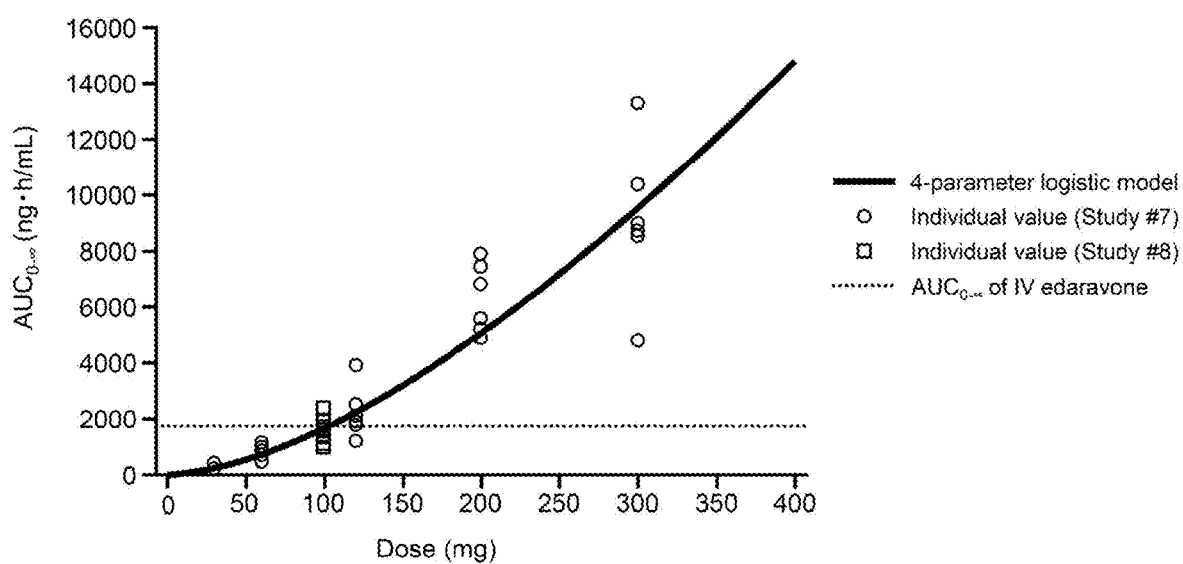
FIG. 4 shows a graph indicating an individual value plot of the $AUCs_{0-\infty}$ vs. edaravone doses and a curve regressed by a 4-parameter logistic model (The circles represent individual values in a study #7, and the squares represent individual values in a study #8. An $AUC_{0-\infty}$ of edaravone upon intravenous administration is indicated by the dotted line using a value upon administration at 60 mg/60 min).

These results are shown in FIG. 4 as an individual value plot of the doses of edaravone and the AUC and a 4-parameter logistic model indicating the relationship between both. In the figure, the horizontal axis is the dose of edaravone and the vertical axis is the AUC. In addition, the value of the AUC (1738 ng·h/mL) of the approved 60-mg edaravone intravenous administration formulation is shown in FIG. 4 with a dotted line. As shown in FIG. 4, the amount of edaravone indicating an AUC similar to the AUC of the 60-mg edaravone intravenous administration formulation was calculated to be within the range of 100 to 105 mg. From this result, the edaravone oral formulation (including the meaning of the edaravone intragastric formulation) maintains an effect similar to that of the approved 60-mg edaravone intravenous administration formulation, for example, by setting the amount of edaravone contained in one administration to 100 to 105 mg and administering orally or via a PEG tube with the timing of administration in an embodiment of the present invention described above and can provide medical care with a reduced burden on patients and caregivers.

Example 7: Effects of Meal Consumption after Administration of Edaravone Oral Formulation on Pharmacokinetics of Edaravone 2

Effects of meal consumption 30 minutes after administration of the edaravone oral formulation on the pharmacokinetics of edaravone were evaluated. Specifically, a clinical study #10 described below was conducted in Japanese healthy adult male subjects. In the clinical study #10, the edaravone oral formulation of the formula #7 (edaravone content of 120 mg) in Table 11 above was used and administered orally once during the study period. In addition, the same standard meal as that used in Example 1 above was used.

Clinical Study #10

As a post-administration consumption group, subjects in fasted conditions after a lapse of 10 hours or longer from meal consumption were orally administered with the edaravone oral formulation, and the standard meal was consumed 30 minutes after the administration. Blood samples were each collected before the administration, and 15 minutes, 30 minutes, 1 hour, 1.5 hours, 2 hours, 4 hours, 6 hours, 8 hours, 12 hours, and 24 hours after the administration, and the concentrations of unchanged edaravone in plasma were measured. The consumption of the standard meal 30 minutes after the administration was carried out after the blood sample collection 30 minutes after the administration, and a subsequent meal was not consumed until the blood sample collection 4 hours after the administration was completed. On the other hand, as a fasted group for reference, the edaravone oral formulation was administered orally to different subjects in fasted conditions, blood samples were collected, and the concentrations of unchanged edaravone in plasma were measured in the same manner. The subjects in the fasted group did not consume a meal either until the blood sample collection 4 hours after the administration was completed. The resulting PK parameters are shown in Table 12 below.

TABLE 12

PK parameters of edaravone due to meal consumption after administration of edaravone oral formulation

| Dose (mg) | Meal condition | Statistics | $t_{max}$ (h) | $C_{max}$ (ng/mL) | $AUC_{0-24\,h}$ (ng · h/mL) | $t_{1/2}$ (h) |
|---|---|---|---|---|---|---|
| 120 | Fasted (n = 6) | Mean | 0.38 | 1735 | 2241.77 | 5.13 |
| | | SD | 0.14 | 738 | 910.63 | 1.46 |
| | 30 min before low-fat meal (n = 6) | Mean | 0.42 | 1953 | 1916.91 | 4.6 |
| | | SD | 0.13 | 838.3 | 383.34 | 0.41 |

A comparison was made between the post-administration consumption group, in which the standard meal was consumed 30 minutes after the administration of the edaravone oral formulation, and the fasted group, in which no meal was consumed for another 4 hours or longer after the administration in fasted conditions. As a result, as shown in Table 12 above, the post-administration consumption group indicated only a slight decrease in the Cmax by about 12.6% and the AUC by about 14.5% in comparison with the fasted group, and no significant difference was observed. Thus, the meal consumption 30 minutes after the oral administration was found to have no effect on the pharmacokinetics of edaravone.

From the above results, when the standard meal was consumed 30 minutes after the administration of the edaravone oral formulation, no significant change was considered to occur in comparison with the fasted conditions. In addition, edaravone was administered as a suspension and thus is presumed to have been rapidly excreted from the stomach, and most of edaravone is presumed to have reached the upper part of the small intestine, which is considered to be the absorption site, by 30 minutes after the administration.

(NG tube), which allows the administration into the stomach via a tube in the same manner, was used as a model of administration via a percutaneous endoscopic gastrostomy tube (PEG tube), and a clinical study #11 described below was conducted. In the clinical study #11, the edaravone oral formulation of the formula #3 shown in Table 1 was used.

Clinical Study #11

The edaravone oral formulation (#3) was administered via a nasopharyngeal gastric tube (NG tube) to the subject group in fasted conditions after a lapse of 10 hours or longer from consumption of a meal. In the administration via an NG tube, first, 100 mL of lukewarm water was injected through an NG tube 1 hour before the administration of the edaravone oral formulation, and 10 mL of lukewarm water was injected through an NG tube immediately before the administration. Then, the edaravone oral formulation was administered to the NG tube, and further 30 mL of water was injected through the NG tube to wash in the edaravone oral formulation. Blood samples were each collected before the administration, and 5 minutes, 15 minutes, 30 minutes, 45 minutes, 1 hour, 1.5 hours, 2 hours, 4 hours, 6 hours, 8 hours, 10 hours, 12 hours, 24 hours, 36 hours, and 48 hours after the administration, and the concentrations of unchanged edaravone in plasma were measured. As a reference example, the same edaravone oral formulation was administered orally to the same subjects, blood samples were collected, and the concentrations of unchanged edaravone in plasma were measured in the same manner. For the oral administration, the edaravone oral formulation was administered orally after a lapse of 10 hours or longer from the previous meal consumption. None of the subjects consumed a next meal until the blood sample collection 4 hours after the administration was completed. The resulting PK parameters are shown in Table 13 below. In addition, results of an analysis of variance conducted on the AUC and Cmax in consideration of the meal condition are shown in Table 14 below.

TABLE 13

PK parameters of edaravone after oral administration and administration via NG tube of edaravone oral formulation

| Administration route | PK parameter | $t_{max}$[a] (h) | $C_{max}$ (ng/mL) | $AUC_{0-t}$ (ng · h/mL) | $AUC_{0-\infty}$ (ng · h/mL) | $t_{1/2}$ (h) |
|---|---|---|---|---|---|---|
| Oral (N = 36) | Mean | 0.5 | 2470 | 2612 | 2657 | 21.52 |
| | CV % | 0.250, 0.500 | 34 | 30.1 | 30.1 | 157.2 |
| Nasopharyngeal gastric tube (N = 36) | Mean | 0.25 | 2775 | 2592 | 2617 | 13.53 |
| | CV % | 0.083, 1.000 | 52.1 | 33.4 | 33.2 | 102.1 |

[a]median, minimum, and maximum

Thus, a difference in the type of meal consumed 30 minutes after the administration is considered to have no effect on edaravone. This suggested that in oral administration of edaravone, edaravone is not affected by a meal after a lapse of 30 minutes from the administration regardless of the type of meal after the administration.

Example 8: Pharmacokinetics of Edaravone in Administration Via Percutaneous Endoscopic Gastrostomy Tube (PEG Tube) 2

Pharmacokinetics of edaravone in administration of the edaravone oral formulation via a PEG tube was evaluated in 36 healthy adults. Specifically, performing gastrostomy in healthy adults is difficult, thus a nasopharyngeal gastric tube

TABLE 14

Ratios of PK parameters determined by analysis of variance and 90% confidence intervals

| Parameter | Units | Least-square mean Nasopharyngeal gastric tube | Oral | Ratio | 90% Confidence interval Lower | Upper |
|---|---|---|---|---|---|---|
| Cmax | ng/mL | 2431 | 2310 | 1.052 | 0.9028 | 1.2267 |
| $AUC_{0-\infty}$ | ng · h/mL | 2501 | 2551 | 0.981 | 0.9307 | 1.0333 |

As shown in Table 13, each PK parameter was very similar regardless of the route of administration, indicating that pharmacokinetics is maintained regardless of the route of administration. As shown in Table 14 above, the analysis of variance indicated that for the least squares mean ratio of the AUC and Cmax of the example administered via an NG tube to the AUC and Cmax of the reference example administered orally, the 90% confidence interval was in the range of 0.8 to 1.25, which is a common criterion for equivalence. This result shows that administration of edaravone into the stomach via an NG tube does not affect the pharmacokinetic parameters AUC and Cmax and can exert an effect of maintaining the pharmacokinetics similar to those in oral administration.

The results of the oral administration in this Example 8 and the results of the administration via a PEG tube in this Example 5 indicated that the Cmax and AUC of edaravone after intragastric administration of the edaravone oral formulation via an NG tube were equivalent to the results after the oral administration of the same edaravone oral formulation. This suggests no difference in the pharmacokinetics of edaravone between intragastric administration via a catheter and oral administration and revealed that sufficient plasma concentration of edaravone is maintained in intragastric administration via a catheter as well as in oral administration. This result with more subjects supports the finding in Example 5 that plasma concentration of edaravone administered via a PEG tube to ALS patients is maintained in a manner similar to the oral administration.

Example 9: Investigation of Adsorption of Edaravone to Catheter In Vitro

In administration using a catheter, catheters of various materials are used in medical facilities. Thus, whether administration is feasible with a catheter of any material was investigated by evaluating adsorption properties of catheters. That is, the edaravone oral formulation (#3) was passed through a catheter, and then the percentage of edaravone collected by washing in with water was evaluated. The types of percutaneous endoscopic gastrostomy tubes (PEG tubes) Nos. 1 to 3 used for the evaluation are shown in Table 15.

TABLE 15

| Types of PEG tubes used for adsorption evaluation | | | |
|---|---|---|---|
| | No. 1 | No. 2 | No. 3 |
| Material | Button: silicone<br>Tubing: polyvinyl chloride | Button: polyurethane<br>Tubing: polyvinyl chloride | Balloon: silicone rubber<br>Tubing: silicone rubber/<br>polyacetal |
| Type | Bumps/button<br>Bump<br>Length: 5.0 cm<br>Diameter: 24 Fr | Bumps/button<br>Bump<br>Length: 5.5 cm<br>Diameter: 24 Fr | Balloon/button<br>Balloon<br>Length: 4.4 cm<br>Diameter: 24 Fr |
| Size | Tubing<br>Length: 60 cm<br>Diameter: outer 6.0 mm<br>inner 4.0 mm | Tubing<br>Length: 30 cm<br>Diameter: outer 5.5 mm<br>inner 3.7 mm | Tubing<br>Length: 60 cm<br>Diameter: outer 5.5 mm<br>inner 3.5 mm |

Specifically, the edaravone oral formulation was loaded into a syringe for catheter administration to give an edaravone amount of 105 mg, and the edaravone oral formulation was passed from the syringe to each of the catheters. Water at a predetermined temperature was then injected into the catheter to wash in the edaravone oral formulation. The edaravone oral formulation that passed through the catheter and the wash-in liquid were collected and mixed, and an amount of edaravone contained in the mixed liquid was measured. The edaravone oral formulation was washed in under any of the following conditions: with 10 mL of water three times, with 30 mL of water at 25° C. or 40° C. once, or with 50 mL of water at 25° C. or 40° C. once. Three measurements were made for each catheter, and the mean and SD of recovery % were calculated. These results are shown in Table 16.

TABLE 16

| | Adsorption evaluation | | |
|---|---|---|---|
| | Type of PEG tube | | |
| Wash-in conditions | No. 1 | No. 2 | No. 3 |
| 10 mL 3 times | 98.0% (0.6) | 100.0% (1.5) | 99.1% (0.6) |
| 30 mL once<br>(Water temperature<br>at 25° C.) | 97.1% (1.5) | 98.6% (1.7) | 97.9% (1.3) |
| 30 mL once<br>(Water temperature<br>at 40° C.) | 101.9% (2.1) | 104.1% (0.7) | 103.0% (0.7) |
| 50 mL once<br>(Water temperature<br>at 25° C.) | 96.5% (1.8) | 97.0% (0.9) | 97.5% (0.4) |
| 50 mL once<br>(Water temperature<br>at 40° C.) | 97.6% (0.8) | 97.9% (0.5) | 95.5% (0.6) |

Shown as mean (SD) of N = 3

As shown in Table 16 above, almost all amount of edaravone was recovered by each specified washing in with water regardless of the material of the catheter used. No adsorption of edaravone was thus observed on the catheters regardless of the material, thus showing that transcatheter administration of the edaravone oral formulation is feasible regardless of the material of the catheter.

A pharmaceutical composition containing edaravone according to an embodiment of the present invention avoids effects of meal consumption on the pharmacokinetics by administration with the most suitable administration interval for each type of meal and exerts excellent effects as the oral formulation or intragastric formulation of edaravone, and thus is useful, for example, for the treatment of oxidative stress diseases.

For a pharmaceutical composition according to an embodiment of the present invention, for example, a time interval from edaravone administration to next meal consumption is 30 minutes or longer.

For a pharmaceutical composition according to an embodiment of the present invention, for example, a time interval from edaravone administration to next meal consumption is 1 hour or longer.

A pharmaceutical composition according to an embodiment of the present invention is, for example, for oral administration.

A pharmaceutical composition according to an embodiment of the present invention is, for example, for intragastric administration.

For a pharmaceutical composition according to an embodiment of the present invention, for example, the intragastric administration is administration via a tube.

For a pharmaceutical composition according to an embodiment of the present invention, for example, the tube is a percutaneous endoscopic gastrostomy tube (PEG tube) or a nasopharyngeal gastric tube (NG tube).

A pharmaceutical composition according to an embodiment of the present invention is, for example, for treating an oxidative stress disease.

For a pharmaceutical composition according to an embodiment of the present invention, for example, the oxidative stress disease is any one of diseases selected from the group of amyotrophic lateral sclerosis, Parkinson's disease, spinocerebellar degeneration, muscular dystrophy, Alzheimer's disease, cerebral infarction, multiple sclerosis, systemic scleroderma, and stomatitis.

For a pharmaceutical composition according to an embodiment of the present invention, for example, the oxidative stress disease is amyotrophic lateral sclerosis.

For a pharmaceutical composition according to an embodiment of the present invention, for example, the time interval is a time interval during an administration period of intermittent or daily administration.

For a pharmaceutical composition according to an embodiment of the present invention, for example, a dose per administration is from 90 to 120 mg of edaravone.

For a pharmaceutical composition according to an embodiment of the present invention, for example, a dose per administration is from 90 to 105 mg of edaravone.

For a pharmaceutical composition according to an embodiment of the present invention, for example, a daily administration frequency is once, and a dose per administration is 105 mg of edaravone.

In a method of administering a pharmaceutical composition according to an embodiment of the present invention, for example, a time interval from edaravone administration to next meal consumption is set to 30 minutes or longer.

In a method of administering a pharmaceutical composition according to an embodiment of the present invention, for example, a time interval from edaravone administration to next meal consumption is set to 1 hour or longer.

In a method of administering a pharmaceutical composition according to an embodiment of the present invention, for example, the pharmaceutical composition is administered orally.

In a method of administering a pharmaceutical composition according to an embodiment of the present invention, for example, the pharmaceutical composition is administered intragastrically.

In a method of administering a pharmaceutical composition according to an embodiment of the present invention, for example, the intragastric administration is administration via a tube.

In a method of administering a pharmaceutical composition according to an embodiment of the present invention, for example, the tube is a percutaneous endoscopic gastrostomy tube (PEG tube) or a nasopharyngeal gastric tube (NG tube).

In a pharmaceutical composition according to an embodiment of the present invention, for example, the pharmaceutical composition is administered to treat an oxidative stress disease.

In a method of administering a pharmaceutical composition according to an embodiment of the present invention, for example, the oxidative stress disease is any one of diseases selected from the group of amyotrophic lateral sclerosis, Parkinson's disease, spinocerebellar degeneration, muscular dystrophy, Alzheimer's disease, cerebral infarction, multiple sclerosis, systemic scleroderma, and stomatitis.

In a method of administering a pharmaceutical composition according to an embodiment of the present invention, for example, the oxidative stress disease is amyotrophic lateral sclerosis.

In a method of administering a pharmaceutical composition according to an embodiment of the present invention, for example, administration of the pharmaceutical composition includes intermittent and daily administrations, and the pharmaceutical composition is administered with the time interval during an administration period of the intermittent or daily administration.

In a method of administering a pharmaceutical composition according to an embodiment of the present invention, for example, a dose of edaravone per administration is from 90 to 120 mg.

In a method of administering a pharmaceutical composition according to an embodiment of the present invention, for example, a dose of edaravone per administration is from 90 to 105 mg.

In a method of administering a pharmaceutical composition according to an embodiment of the present invention, for example, a frequency of a daily dose is once, and a dose of edaravone per administration is 105 mg.

An oral formulation is desired to be provided, as it is less burdensome for patients and caregivers and is preferred in terms of QOL. To meet such a demand, an oral formulation of edaravone is being developed through clinical and other studies (WO 2020/091036). The entire contents of this publication are incorporated herein by reference.

With respect to therapeutic agents for an oxidative stress disease, the same agent may have different conditions under which the agent can effectively exert its effect depending on administration methods of the agent. In addition, an oral formulation of edaravone is still under development, and conditions under which the same effect as that of the injection is achieved has not been elucidated.

Thus, one object of the present invention is to provide a pharmaceutical composition containing edaravone as an active ingredient for oral administration and equivalent administration.

A pharmaceutical composition according to an embodiment of the present invention contains edaravone as an active ingredient. The pharmaceutical composition is administered to a subject orally or intragastrically with any one of time intervals 1) to 3) below:

1) in a case where the subject has consumed a high-fat meal, 8 hours or longer after the consumption;
2) in a case where the subject has consumed a standard meal, 4 hours or longer after the consumption; and
3) in a case where the subject has consumed a light meal, 2 hours or longer after the consumption.

A method of administering an edaravone-containing pharmaceutical composition according to an embodiment of the present invention includes administering a pharmaceutical composition containing edaravone as an active ingredient to a subject orally or intragastrically with any one of time intervals 1) to 3) below:

1) in a case where the subject has consumed a high-fat meal, 8 hours or longer after the consumption;
2) in a case where the subject has consumed a standard meal, 4 hours or longer after the consumption; and
3) in a case where the subject has consumed a light meal, 2 hours or longer after the consumption.

For drugs exhibiting high solubility and high permeability and classified as BCS Class 1, meal consumption has little effect on pharmacokinetics, such as bioavailability, when the drugs are administered orally (Pharmaceutical Research, Vol. 22, No. 1, 11-23, 2005).

Edaravone is classified as a high solubility compound and also classified as a high permeability compound based on the results of a membrane permeability test using Caco-2 cells shown in Example 3 described above. Thus, edaravone is regarded as a BCS Class 1 drug with high solubility and high permeability. These findings led to a brief that edaravone is a compound whose pharmacokinetics are not affected by meal consumption.

The Examples described above, nevertheless, show that consumptions of meals prior to administration affect the pharmacokinetics of edaravone. Not only the presence or absence of a meal but also the types of meal cause differences in effects on the pharmacokinetics of edaravone, and suitable administration timing depends on each type of meal.

An embodiment of the present invention determines, for each type of meal, a time interval after a meal to administration and thus, for example, avoids effects of a meal on pharmacokinetics such as bioavailability in both oral administration and intragastric administration of edaravone. Thus, a pharmaceutical composition according to an embodiment of the present invention exhibits an excellent therapeutic effect on oxidative stress diseases as a formulation for oral administration (also referred to as an "oral formulation" above) or a formulation for intragastric administration (also referred to as an "intragastric formulation" above) similarly to an injection administered intravenously. In addition, a pharmaceutical composition according to an embodiment of the present invention is administered orally or intragastrically and thus further reduces the burden on patients and caregivers.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of reducing oxidative stress in a subject in need thereof, comprising:
orally or intragastrically administering, to a subject in need thereof, a liquid pharmaceutical composition comprising edaravone with a first time interval from a consumption of a meal by the subject in need thereof to an administration of the liquid pharmaceutical composition to the subject in need thereof such that the first time interval achieves the same pharmacokinetics as administration of the liquid pharmaceutical composition by the same method to the subject under a fasting condition of 10 hours or longer and that the same pharmacokinetics includes Cmax and AUC,
wherein the liquid pharmaceutical composition is administered to the subject in need thereof such that a dose of edaravone per administration is in a range of 90 to 120 mg, the first time interval for the consumption of a high-fat meal in a range of 800 to 1000 calories with 50% fat is 8 hours before the administration of the liquid pharmaceutical composition to the subject in need thereof, the first time interval for the consumption of a standard meal in a range of 400 to 500 calories with 25% fat is 4 hours before the administration of the liquid pharmaceutical composition to the subject in need thereof, and the first time interval for the consumption of a light meal of 250 calories is 2 hours before the administration of the liquid pharmaceutical composition to the subject in need thereof.

2. The method of claim 1, further comprising:
setting a second time interval from the administration of the liquid pharmaceutical composition to a consumption of a next meal by the subject in need thereof such that the second time interval is 30 minutes or longer after the administration of the liquid pharmaceutical composition.

3. The method of claim 1, further comprising:
setting a second time interval from the administration of the liquid pharmaceutical composition to a consumption of a next meal by the subject in need thereof such that the second time interval is 1 hour or longer after the administration of the liquid pharmaceutical composition.

4. The method of claim 1, wherein the administration of the liquid pharmaceutical composition is oral administration.

5. The method of claim 1, wherein the administration of the liquid pharmaceutical composition is intragastric administration.

6. The method of claim 5, wherein the intragastric administration is administration via one of a percutaneous endoscopic gastrostomy catheter and a nasopharyngeal gastric catheter.

7. The method of claim 1, wherein the liquid pharmaceutical composition includes a dispersant.

8. The method of claim 1, wherein the liquid pharmaceutical composition includes a dispersant, a thickener and a stabilizer.

9. The method of claim 1, wherein the oxidative stress to be reduced is caused by at least one disease selected from a group of amyotrophic lateral sclerosis, Parkinson's disease, spinocerebellar degeneration, muscular dystrophy, Alzheimer's disease, cerebral infarction, multiple sclerosis, systemic scleroderma, and stomatitis.

10. The method of claim 9, wherein the oxidative stress disease is amyotrophic lateral sclerosis.

11. The method of claim 1, wherein the liquid pharmaceutical composition is administered to the subject in need thereof intermittently or daily such that the first time interval is a time interval during an administration period of an intermittent or daily administration.

12. The method of claim 1, wherein the liquid pharmaceutical composition is administered to the subject in need thereof such that a dose of edaravone per administration is in a range of 90 to 105 mg.

13. The method of claim 1, wherein the liquid pharmaceutical composition is administered to the subject in need thereof such that a dose of edaravone per administration is in a range of 100 to 105 mg.

14. The method of claim 1, wherein the liquid pharmaceutical composition is administered to the subject in need thereof such that a frequency of a daily administration is once and that a dose of edaravone per administration is 105 mg.

\* \* \* \* \*

UNITED STATES PATENT AND TRADEMARK OFFICE
CERTIFICATE OF CORRECTION

PATENT NO. : 11,911,366 B2
APPLICATION NO. : 17/564538
DATED : February 27, 2024
INVENTOR(S) : Hidetoshi Shimizu et al.

Page 1 of 1

It is certified that error appears in the above-identified patent and that said Letters Patent is hereby corrected as shown below:

In the Claims

Column 33, Line 57:
"to a subject in" should read -- to the subject in --.

Signed and Sealed this
Twenty-fifth Day of March, 2025

Coke Morgan Stewart
*Acting Director of the United States Patent and Trademark Office*